(12) United States Patent
Butt et al.

(10) Patent No.: US 8,697,376 B2
(45) Date of Patent: Apr. 15, 2014

(54) SYNTHETIC PROTEASE SUBSTRATES, ASSAY METHODS USING SUCH SUBSTRATES AND KITS FOR PRACTICING THE ASSAY

(75) Inventors: Tauseef R. Butt, Malvern, PA (US); Joseph Manimala, Silver Spring, MD (US); Mabel A. Cejas, Oreland, PA (US); James E. Strickler, Havertown, PA (US); William Kingsbury, Wilmington, NC (US); Jian Wu, Frazer, PA (US)

(73) Assignee: Lifesensors, INc., Malvern, PA (US)

( * ) Notice: Subject to any disclaimer, the term of this patent is extended or adjusted under 35 U.S.C. 154(b) by 173 days.

(21) Appl. No.: 13/020,416

(22) Filed: Feb. 3, 2011

(65) Prior Publication Data
US 2011/0319293 A1    Dec. 29, 2011

Related U.S. Application Data

(60) Provisional application No. 61/300,987, filed on Feb. 3, 2010.

(51) Int. Cl.
*G01N 33/573*  (2006.01)
*C40B 40/00*  (2006.01)
*C07K 5/02*  (2006.01)
*A61K 38/16*  (2006.01)

(52) U.S. Cl.
USPC ............. 435/7.4; 435/7.5; 435/212; 530/300; 530/350; 506/11; 506/18

(58) Field of Classification Search
USPC ............ 435/7.4, 7.5, 212; 503/300, 331, 350; 506/11, 18
See application file for complete search history.

(56) References Cited

U.S. PATENT DOCUMENTS

2003/0037350 A1*  2/2003  Glucksmann et al. ............. 800/8
2004/0009553 A1*  1/2004  Glucksmann et al. ........ 435/69.1
2005/0053954 A1*  3/2005  Brennan et al. ................... 435/6

OTHER PUBLICATIONS

Kingsbury et al. Int. J. Peptide Protein Research (1986) 27: 659-665.*
Kingsbury et al. Proc. Nnatl. Acad. Sci. (1984) 81: 4573-4576.*
STN Registry file for Ubiquitin protease downloaded Apr. 17, 2013.*
Hermann et al. Chemistry of Peptides and Proteins (1993) 5/6(Part A): 109-114.*
Brown et al. Anal. Biochem. (1987) 161: 219-225.*

* cited by examiner

*Primary Examiner* — Susan Hanley
(74) *Attorney, Agent, or Firm* — Patrick J. Hagen; Dann, Dorfman, Herrell and Skillman, P.C.

(57) ABSTRACT

Synthetic protease substrates and methods which facilitate the identification of substrates of a protease, particularly ubiquitin, ubiquitin-like, or proteasome protein are provided.

33 Claims, 6 Drawing Sheets

SYNTHETIC PROTEASE SUBSTRATES, ASSAY METHODS USING SUCH SUBSTRATES AND KITS FOR PRACTICING THE ASSAY

CROSS-REFERENCE TO RELATED APPLICATIONS

The present application claims the benefit of U.S. Provisional Patent Application No. 61/300,987, filed Feb. 3, 2010, the entire disclosure of which is incorporated by reference herein.

FIELD OF THE INVENTION

The present invention relates to the field of molecular biology. More specifically, the invention provides protease substrates chemically modified to include one or more detectable labeling moieties, as well as highly sensitive assays for a variety of proteases, in which the labeling moieties are released and detected following cleavage of the scissile bond within the substrate molecule.

BACKGROUND OF THE INVENTION

Regulation of protein content in a cell is a delicate balance between the synthesis of new proteins and the degradation of obsolete, old, defective, or misfolded proteins by the proteasome complex. The cell targets proteins for proteasomal degradation through the attachment of ubiquitin (Ub), an 8,500 Da protein, which is highly conserved among all living organisms. The attachment of ubiquitin to a protein involves the coordinated action of three ligases designated as E1, E2 and E3 that join the C-terminus of ubiquitin to the ε-amino group of a Lys residue in the protein to form an isopeptide bond. (Hershko et al. (1998) Ann. Rev. Biochem. 425). The signal is reinforced by the addition of several more Ubs (usually by conjugating each new Ub to lysine-48 (or K-63 or K-29) of the previous molecule), creating a poly-Ub tag. Proteins having this poly-Ub tag are delivered to the proteasome, which hydrolyses the polypeptide into short oligopeptides and releases free Ub allowing it to be recycled (Ciechanover (1998) EMBO J. 17:7151). The E3 Ub ligase primarily determines the substrate specificity of the polypeptide ubiquitylation (Pickart (2001) Ann. Rev. Biochem. 70: 503; Hershko et al. (1998) Ann. Rev. Biochem. 425). It is important to note that not every Ub attachment results in the formation of a poly-Ub tagged protein and subsequent targeting to the proteasome. Attachment of a single Ub molecule to its target protein can modulate activity or localization, or can play a role in signal transduction (Hicke (2001) Nat. Rev. Mol. Cell. Biol. 2:195). Proteasomes (26S) are multicomponent particles consisting of a 20S core complex containing alpha and beta subunits and capped at either end by 19S regulatory complexes which control the entry of target proteins into the catalytic 20S core. Protein degradation is carried out by three proteases, β1, β2, and β5 (2 copies each per 20S core), which function as caspase-like, trypsin-like, and chymotrypsin-like activities, respectively. (Fang, et al. (2004) Cell Mol Life 61:1546; Hendil et al. (2004) Current Protein and Peptide Science 5:135; Rivett et al. (2004) Curr. Prot. Pept. Sci. 5:133; Rivett et al. (2004) 5:153).

The ultimate fate of Ub-tagged proteins is dictated by de-ubiquitylating enzymes (DUBs), a class of proteases known as isopeptidases, which function to salvage proteins from degradation by removing Ub or ubiquitin-like protein (Ubls). Thus, it will be appreciated that over expression of DUBs causes a buildup of proteins and under expression or malfunction results in enhanced degradation of essential proteins. There have been intensive studies on Ub and protein degradation in neuronal function showing Ub to be a component of proteinaceous deposits in neurodegenerative disorders (e.g., neurofibrillary tangles of Alzheimer's disease, Lewy bodies of Parkinson's disease, and Pick bodies of Pick's disease (Yi et al. (2007) Pharm. Rev. 59:14.)) Since DUBs play a key role in the Ub degradation pathway, it is widely believed that they also play a role in these disorders (Mori et al. (1987) Science 235:1641; Lowe et al. (1988) Neurosci. Letters 94: 203; Lowe et al. (1988) J. Pathol. 155:9.

DUBs are typically cysteine proteases and can be divided into two general classes: Ub C-terminal hydrolases (UCH), and Ub processing proteases (UBP), also referred to as Ub-specific proteases (USP). The major class of DUBs, the UBP (USP) family, consists of larger proteins (41 kDa and above) that exhibit no homology to UCHs, and cleave Ub from a wide range of protein substrates (Chung and Baek (1999) Biochem. Biophys. Res. Commun. 266:633; D'Andrea et al., (1998) Crit. Rev. Biochem. Mol. Biol. 33:337; Wilkinson (1997) FASEB J. 11:1245; Wilkinson and Hochstrasser (1998) Ubiquitin and the Biology of the Cell, Plenum Press: New York, 99). In addition to the classical UBP/USP enzymes are enzymes capable of removing Ub-like proteins (Ubls) from a protein substrate (see Tables 1 and 2; see also Jentsch and Pyrowolakis (2000) Trends Cell Biol., 10:335-42; Muller et al. (2001) Nat. Rev. Mol. Cell. Biol., 2:202-10; see also U.S. Pat. No. 7,060,461 and U.S. patent application Ser. No. 10/504,785). Ubls include, without limitation, ubiquitin, RUB1, HUB1, ISG15, FUB 1, NEDD 8, FAT 10, SUMO-1, SUMO-2, SUMO-3, Apg 8, Apg 12, Urm1, UBL 5 and Ufm1. The Ubl proteases are specific for Ubls, and include for example, yeast Ulp1 and Ulp2 (Li and Hochshasser (2000) Mol. Cell. Biol. 20: 2367; Li and Hochshasser (1999) Nature 398: 246), and human SENP1 and SENP2 (Kamitani et al. (1997) J. Biol. Chem. 272: 14001; Kamitani, et. al. (1998) J. Biol. Chem. 273: 11349), all of which are specific for Small Ub-like Modifier (SUMO) conjugates. Other known Ulps include DEN1 (SENP8), which deconjugates the UBL NEDD8 from protein substrates (Gan-Erdene et. al. (2003) J. Biol. Chem. 278:28892; Hemelaar et. al. (2004) Mol. Cell. Biol. 24:84) and UBP43 (USP18) protease, which cleaves interferon induced UBL ISG15 conjugates (Malakhov et. al. (2002) J. Biol. Chem. 277:9976; Knobeloch et. al. (2005) Mol. Cell. Biol. 25:11030). ISG15 is actively conjugated and de-conjugated by a variety of enzymes. Genomics has identified at least 700 human genes that putatively encode enzymes involved in Ub conjugation and de-conjugation. Of these enzymes, at least 100 are believed to encode functional DUBs, some of which have multiple isoforms (Nijman et. al. (2005) Cell 123:773; Wong et. al. (2003) Drug Discov. Today 8). The high degree of diversity among the DUBs and the fact that members of this family have characteristic developmental expression patterns (Park et. al. (2000) Biochem. J. 349 (Pt. 2):443), biochemical properties (Layfield et. al. (1999) Anal. Biochem. 274:40), cellular localization patterns (Cai et al. (1999) PNAS 96:2828; Lin et. al. (2000) Mol. Cell. Biol. 20:6568), tissue distributions (Park et. al. (2000) Biochem. J. 349 (Pt. 2):443; Lin et. al. (2000) Mol. Cell. Biol. 20:6568), preferred targets (Lin et. al. (2001) J. Biol. Chem. 276:20357; Wilkinson (2000) Semin. Cell Dev. Biol. 11:141; Li et. al. (2002) Nature 416:648) and cellular functions (Chung et al. (1999) Biochem. Biophys. Res. Commun. 266:633; Hochstrasser (1996) Annu. Rev. Genet. 30:405; Weissman (2001) Nat. Rev. Mol. Cell. Biol. 2: 169) point to the importance of this pathway in both health and disease.

TABLE 1

Properties of Ubiquitin-like Proteins (Ubls)

| Ubls | Function | Knockout phenotype | Substrate | % UB Identity | KDa | Hydrolase | COOH Residues |
|---|---|---|---|---|---|---|---|
| Ub | Translocation to proteasome | not viable | many | 100 | 8.5 | Numerous | LRLRGG |
| SUMO (SMT3) | Translocation to nucleus | not viable | RanGap, many others | 18 | 11.6 | Ulp1/Ulp2 | GG |
| RUB1 (NEDD8) | Regulation of mitosis. | viable; non-essential. | Mostly cullins | 60 | 8.7 | Den1/Ulp8 | GG |
| HUB1 | Cell polarization. | viable; deficient in mating. | Sph1, Hbt1, cell polarity factors | 22 | 8.2 | not known | YY |
| ISG15 (UCRP) | Interferon αβ responses, immune regulation | IFN, LPS hypersensitivity; death | PLCγ1, Stat1, many others | ~30; 28 two domains | 15.0 | UBP43 (USP18) | LRLRGG |
| APG12 | Autophagy | viable, defective in autophagy | Apg5 | 18 | 21.1 | not cleaved | FG |
| URM1 | Unknown | ts growth; non-essential. | unknown | 20 | 11.0 | not known | GG |
| APG8 (LC3) | Autophagy | viable; no autophago-cytosis or sporulation | phospatidyl-ethanol-amine | 18 | 13.6 | Apg4/Aut2 | FG |
| FAT10 | Interferon γ responses | unknown | unknown | ~41; 30 two domains | 15 | not known | GG |
| Ubi-L (Fau) | immune regulation | unknown | unknown | 35 | 8.3 | not known | GG |

TABLE 2

SUMO Hydrolases/Proteases

| Enzyme | Properties | Reference |
|---|---|---|
| UB1-specific Protease ULP1 | 72 KDa. 621 residues Cleaves linear fusion and SUMO isopeptides bonds. | Li and Hochstrasser (1999) Nature398: 246-51 |
| ULP2 (Yeast) | 117 KDa, 1034 residues Cleaves linear fusions and SUMO isopeptide structures. | Li and Hochstrasser (2000) Mol. Cell. Biol., 20: 2367-77 |
| SUMO-I C-Terminal | 30 Kda Cleaves linear fusions and SUMO isopeptide structures | Suzuki et al. (1999) J. Biol. Chem., 274: 31131-4 |
| SUMO-I specific Protease SUSP I (Human) | 126 KDa 1112 residues Specific for SUMO-1 fusion but not Smt3 fusion. Does not cleave isopeptide bond. | Kim et al. (2000) J. Biol. Chem., 275: 14102-6 |
| Sentrin specific Proteases (SENP) SENP1, SENP2 SENP3, SENP4 SENP5, SENP6 SENP7 | All of the SENP enzymes have conserved C-terminal region with core catalytic cysteine. The smallest SENP7 is 238 residues and the largest SENP6 is 1112 residues. | Yeh et al. (2000) Gene, 248: 1-14; Gong, et al. (2000) J. Biol. Chem., 275: 3355-9 |

DUBs have been implicated in many diseases (see Table 3). For example, evidence has linked the DUB ataxin-3 to Machado-Joseph disease or spinocerebellar ataxia type 3, as overexpression of this DUB causes a buildup of a variety of proteins in the endoplasmic reticulum-associated degradation (ERAD) pathway (Zhong et al. (2006) Hum. Mol. Genet. 15:2409). The DUB UCH-L1 is associated with Parkinson's disease (Meray et al. (2007) J. Biol. Chem., 282: 10567), while USP14 is associated with ataxia (Crimmins et al. (2006) J. Neurosci. 26:11423). Also, USP20 (VDU2; von Hippel-Lindau interacting protein 2), which de-ubiquitylates and stabilizes the hypoxia inducible factor HIF-1α, is overexpressed in certain tumors (Li et. al. (2005) EMBO Rep. 6:373; Powis et al. (2004) Mol. Cancer. Ther. 3:647). USP2a has been implicated in controlling the half-life of fatty acid synthetase (FAS) that is oncogenic to prostate tissue (Graner et al. (2006) Cancer Cell. 14:1293). By inhibiting de-ubiquitylation of FAS, the protein is degraded by the proteasome and the growth of cancer tissue is blocked (Graner et al. (2006) Cancer Cell. 14:1293). In addition, USP7 (HAUSP) plays a key role in regulating the ubiquitylation of the mouse RING-finger E3 ligase Mdm2 (and its human homolog Hdm2) (Li et. al. (2004) Mol. Cell. 13:879; Cummins et. al. (2004) Nature 428:1). Hdm2 binds the tumor suppressor p53 and poly-ubiquitylates it, thereby facilitating its degradation by the proteasome (Honda et al. (1997) FEBS Lett. 420:25; Haupt et. al. (1997) Nature 387:296; Fang et. al. (2000) J. Biol. Chem. 275:8945; Teoh et. al. (1997) Blood 90:1982). In addition to these conditions, DUBs are associated with aneurismal bone cyst (Oliveira et al. (2006) J. Clin. Oncol. 24: e1:e2), retinal degeneration (Sano et al. (2006) Amer. J. Path. 169:132), plague (Cornelis (2000) PNAS (USA) 97:8778), Parkinsonism (Li et al. (2006) Hum. Mutat. 27:1017), ataxia (Crimmins et al. (2006) J. Neurosci. 26:11423), and diabetes (Jaberi (2004) Asia Pacific J. Clin. Nutr. 13).

TABLE 3

DUBs and their roles in various physiological conditions.

| Physiological Conditions | Associated DUBs |
|---|---|
| Neuro-degeneration | USP31 (Tzimas et al. (2006) Cell Signal 18: 83) |
| | USP14 (Ehlers (2003) Trends Neurosci. 26: 4) |
| | Ataxin 3 (Rub et al. (2006) Brain Pathol. 16: 218) |
| | UCH-L1 (Setsuie et al. (2007) Neurochem Int.50: 119) |
| Cancer | CYLD1 (Biggs et al. (1996) Oncogene 12: 1375) |
| | UCH-L1 (Yang et al. (2006) Acta Biochim Biophys Sin. 38: 602) |
| | USP2 (Graner et al. (2004) Cancer Cell 5: 253) |
| | USP7 or HAUSP (Cheon (2006) Int. J. Oncol. 28: 1209) |
| | USP18 or UBP43 (Kang et al. (2001) Gene 267: 233) |
| | USP20 (Li et al. (2002) Biochem. Biophys. Res. Commun. 294: 700) |
| | USP33 (De Pitta (2005) Haematologica 90: 890) |
| | USP1 (Nijman et al. (2005) Mol. Cell 17: 331) |
| | USP9Y (Dasari et al. (2001)J. Urol. 165: 1335) |
| | USP9X (Rolen et al. (2006) Mol. Carcinog. 45: 260) |
| | CYLD (Zhang et al. (2006) J. Clin. Invest. 116: 3042) |
| | YOPJ (Lemaitre et al. (2006) Infect. Immun. 74: 5126) |
| | DUB2 (Migone et al. (2001) Blood 98: 1935) |
| | USP42 (Paulsson et al. (2006) Leukemia 20: 224) |
| | EIF3S3 (Savinainen et al. (2006) Prostate 66: 1144) |
| | USP10 (Deng et al. (2006) Breast Cancer Res.) |
| | USP25 (Deng et al. (2006) Breast Cancer Res.) |
| | TNFAIP3 (Chen (2004) Cancer Res. 64: 8135) |
| | USP36 (Kim et al. (2005) Biochem. Biophys. Res. Commun. 330: 797) |
| | USP4 (Velazquez-Fernandez et al. (2005) Surgery 138: 1087) |
| | USP22 (Glinsky (2006) Cell Cycle 5: 1208) |
| | USP14 (Shinji et al. (2006) Oncol. Rep. 15: 539) |
| | UBPY or USP8 (Alwan et al. (2007) J. Biol. Chem. 282: 1658) |
| Hematological | USP1 (Nijman et al. (2005) Mol. Cell 17: 331) |
| | DUB-1 (Kriplani et al. (2006) J. Obstet. Gynaecol. 26: 673) |
| | DUB-2 (Matytsina et al. (2006) Prim. Care 33: 503) |
| Muscle formation | UBP45 (Park et al. (2002) PNAS 99: 9733) |
| | UBP69 (Park et al. (2002) PNAS 99: 9733) |
| Infertility | USP9X (Xu et al. (2005) Eur. J. Neurosci. 21: 3017) |
| | USP9Y (Krausz et al. (2006) Hum Mol. Genet. 15: 2673) |
| | USP26 (Ravel et al. (2006) Mol. Hum. Reprod. 12: 643) |
| Viral Infection | UL36 (Bottcher et al. (2006) J. Virol. 80: 9910) |
| | pUL48(Wang et al. (2006) J. Virol. 80: 6003) |

Many neurodegenerative diseases (NDDs) including Alzheimer's (AD), Parkinson's, Huntington's, prion disease, amyotrophic lateral sclerosis, and spinocerebellar ataxia (SCA) are characterized by alterations in protein folding, post-translational modifications, trafficking, and degradation that produce neuronal dysfunction and death. These diseases ultimately result in the formation of pathologically distinct and disease-specific protein aggregates, including Ub (Ross et al. (2004) Nat. Med. 10 Suppl1:S10). Neurofibrillary tangles and amyloid plaques contain elevated wild-type or mutant Ub levels, raising the possibility that dysfunctions in the Ub proteasome system (UPS), specifically those involving DUBs, contribute to AD pathogenesis and progression (Sherman et al. (2001) Neuron 29:15; van Leeuwen et al. (2006) Biochem. Soc. Trans. 34:738). Molecular misreading during translation leads to the formation of UBB+1, a mutant Ub containing a 19 amino acid C-terminal extension that is incapable of ubiquitylating substrates (van Leeuwen et al. (2000) Ann. N Y Acad. Sci. 908:267; Trower et al. (1996) PNAS (USA) 93:1366).

Another neuronal- (and testes-) specific DUB, Ub C-terminal hydrolase L-type (UCH-L) is also oxidatively modified, less soluble than normal, and associated with pathological lesions in AD brains (Choi et al. (2004) J. Biol. Chem. 279:13256). Recent data from Gong et al. suggests that increasing UCHL1 activity prevents synaptic dysfunction and memory loss associated with AD. This provides a direct link between DUB activity and AD pathogenesis (Gong et al. (2006) Cell 126:775). Ub buildup has also been shown in brains of patients with frontotemporal dementia, a disorder linked to chromosome 17 (van der Zee et al. (2007) Hum. Mutat. 28:416; Cruts et al. (2006) Curr. Alzheimer Res. 3:485; Cruts et al. (2006) Nature 442:920; Pirici et al. (2006) J. Neuropathol. Exp. Neurol. 65:289; van der Zee et al. (2006) Brain 129:841; Whitwell et al. (2007) Arch. Neurol. 64:371;

Josephs et al. (2007) J. Neuropathol. Exp. Neurol. 66:142; Dachsel et al. (2006) Acta Neuropathol (Berl); Gass et al. (2006) Hum. Mol. Genet. 15:2988; Mackenzie et al. (2006) Brain 129:853).

The ataxia gene encodes DUB-USP14 with mutation in this gene leading to synaptic transmission and plasticity deficits before aggregate formation occurs (Wilson et al. (2002) Nat. Genet. 32:420). These data provide a linkage between DUB activity, synaptic maintenance, and cognitive performance, as well as a direct correlation between MCI or pre-pathological AD and the UPS. UPS efficiency decreases with aging and its efficacy is most diminished in brain regions first susceptible to AD pathogenesis (hippocampus and inferior parietal cortex) (Keller et al. (2002) Ageing Res. Rev. 1:279; Keck et al. (2003) J. Neurochem. 85:115). These data provide a linkage between very early AD (or MCI) and UPS dysfunction that needs to be explored in greater detail. Several indirect and direct UPS and DUB-specific mechanisms that play important roles in the development and progression of NDD have been identified (Ciechanover et al. (2003) Neuron 40:427); however, these data are only beginning to scratch the surface of NDD research. Numerous unasked or unanswered questions remain. A comprehensive microarray analysis of DUB proteins found in the CSF of control and NDD patients will identify novel DUBs that are affected in NDDs. These DUBs may serve as targets for basic NDD research protocols and provide novel avenues for drug discovery.

A variety of chronic diseases, among them certain of the above-mentioned NDDs, such as Alzheimer's and Parkinson's disease, inflammatory conditions (Savitt et al. (2006) J. Clin. Invest 116:1744; Egerer et al. (2002) 29:2045), IBD (Crohn's disease and ulcerative colitis) (Anderson et al. (2006) Drug Resist Updates 9:198; Cheroni et al. (2009) Hum. Molec. Gen. 18:82; Shaw et al. (2007) 6:295; Schmidt et al. (2010) Gut. 59:896) and an increasing number of malignancies (Ludwig et al. (2005) Cancer 104:1794) have been shown to correlate with altered proteasome content and/or activity. While usually not the precipitating event of the disease, proteasome alterations are often a reflection of genetic or environmental effects on gene expression that ultimately involve the ubiquitin system in removal of defective proteins or accumulation of certain of these proteins (Savitt et al. (2006) J. Clin. Invest 116:1744; Schmidt et al. (2010) Gut. 59:896; Keller et al. (2005) J. Neurochem. 75:436). In addition, infectious agents such as viruses may stimulate production of interferon γ (IFNγ), thereby inducing a specialized form of proteasome (the immunoproteasome) which is involved in processing of internally generated antigenic epitopes for display with MHC I on the cell surface (Rivett et al. (2004) Curr. Prot. Pept. Sci. 5:133; Rivett et al. (2004) Curr. Prot. Pept. Sci. 5:153; Yewdell et al. (2005) PNAS 102:9089; Heink et al. (2005) PNAS 102:9241) for recognition by T cells.

Accumulation of Ub tagged proteins leads to formation of protein plaques and induction of apoptosis. This phenomenon has been used to advantage in the treatment of multiple myeloma through the introduction of the proteasome inhibitor bortezomib (Velcade). Bortezomib is the first-in-class FDA approved drug that functions through inhibition of the proteasome. Its success has stimulated major research efforts in both academia and in the pharmaceutical industry aimed at the design of less toxic, more potent inhibitors of the proteasome for the treatment of neurodegeneration, cancer, musculoskeletal, and autoimmune diseases.

Thus proteasome alterations may be considered as a possible biomarker for early detection of specific diseases or physiological states in a cell (Anderson et al. (2006) Drug Resist Updates 9:1998; Shaw et al. (2007) Nature Reviews Drug Discovery 6:295; Ducoux-Petit et al. (2008) J. Proteome Res. 7:2852; Sun et al. (2006) Neoplasia 8:645), especially in situations where there is a familial component to the disease and where early diagnosis and/or treatment leads to improved outcomes (AD and PD especially; Shaw et al. (2007) Nature Reviews Drug Discovery 6:295).

The role of proteasomes, Ub and various proteasomal and Ub pathway enzymes in multiple cellular and metabolic processes, as well as in various disease states, continues to be revealed. However, a substantial amount of work is still necessary to uncover all of their roles in sustaining homeostasis. A major challenge that needs to be overcome is the lack of an adequate system to assay these enzymes. The enzyme activity assays currently available have some notable shortcomings. For example, none of these can reliably measure the catalytic activity of DUBs immobilized on a solid support in a multiplex environment using a single dye, chromophore or fluorophore. Another limitation of prior assays is that not all DUBs recognize one specific substrate. Nature has evolved about 100 DUBs capable of cleaving different classes of ubiquitylated proteins. Also, certain regents employed in prior assays require specialized plate readers for analysis. Nor do such assays provide reagents useful for tissue staining.

With the exception of kinase assays, in general, very few catalytic activity assays are available for immobilized enzymes in multiplex environment and none is available for detecting DUBs in tissue samples. Currently, the only way to detect DUBs in tissue samples is by immunohistochemistry. This method only detects the presence of DUB protein, but provides no information about DUB protein activity. This method is only as efficient as the specificity and, to an extent, the binding affinity of the antibody. An enzyme activity assay is a better indicator of the presence of these enzymes, assuming that they are active in the tissue.

A number of assays have previously been described that allow the measurement of DUB activity in solution. A. Shanmugham and H. Ovaa, (2008) Curr. Opin. Drug Discov. Devel., 11: 688. Commercially available assays of this kind include: Ubl-AMC assay, (Dang, (1998) Biochemistry, 37: 1868), and Lanthascreen TR assay (Gururaja et al. (2005), Methods Enzymol., 399: 663). The Ubl-AMC assay is a coumarin based fluorogenic assay, in which coumarin is covalently linked to the C-terminal of the Ub to form 7-amido-4-methylcoumarin (AMC). The resulting amide bond changes the fluorescence property of coumarin and it only becomes fluorescent (excitation at 380 nm and emission at 460 nm) upon cleavage by the DUB. The coumarin is released into the solution and the resulting fluorescence is proportional to the DUB activity. The Lanthascreen TR assay is a FRET-based assay in which the substrate consists of Ub in which the N-terminus is modified with green fluorescent protein (GFP), and the C-terminus is modified with terbium chelate. The intact substrate shows a high degree of Förster Resonance Energy Transfer (FRET), but upon cleavage by DUBs, the FRET diminishes and the fluorescence signal at 520 nm becomes weaker. The signal at 520 nm is inversely proportional to the DUB activity. Not all DUBs recognize the aforementioned substrates. Thus, although there are DUBs that cleave Ub-AMC, or Ub-GFP, there are DUBs that don't recognize any one of them or recognize them very poorly.

The aforementioned solution phase assays cannot be adapted to test immobilized DUBs, since the cleavage products are soluble. Previously described substrates such as ubiquitin vinylsulfone (or the related vinylmethyl ester) would allow labeling in a microarray format. (Bogyo, McMaster et al., (1997) PNAS (USA), 94: 6629; Bogyo, Shin et al., (1998)

Chem. Biol., 5: 307; Borodovsky, Ovaa et al., (2002) Chem. Biol., 9: 1149; Love, Pandya et al., (2009) ACS Chem. Biol., 4: 275. These substrates, however, have two distinct disadvantages. First, localization of the reacted species requires the use of either an anti-Ub antibody or an antibody directed to an artificially attached tag such as the flag-tag or the HA-epitope. This will increase the likelihood of non-specific labeling on an array. Second, and more importantly, the vinylsulfone moiety will react with any free thiol available, independent of the activity of the labeled DUB. Indeed, vinylsulfones are commonly used to modify proteins through free or introduced cysteine residues (Liu and Hanzlik, (1992) J. Med. Chem., 35: 1067; Palmer, Rasnick et al., (1995) J. Med. Chem., 38: 3193). Vinylsulfones contain a Michael acceptor, which under appropriate conditions will be subject to nucleophilic attack by primary amines. That ubiquitin vinylsulfones show specificity for DUBs is probably due to the recognition and binding of the ubiquitin moiety by the DUB and subsequent orientation of the vinyl group adjacent to the active site cysteine.

Currently available methods for detecting changes in proteasome content or activity involve complicated and expensive techniques and instrumentation for proteasome isolation and evaluation, including CE-MS, enzyme assays, or immunohistochemical analysis using antibodies to specific PS components from biopsy and/or autopsy samples (Sun et al. (2006) Neoplasia 8:645; Xu et al. (2006) Biochem. Biophys. Acta. 1764:1940; Majetschake et al. (2008) J. Immunol. Methods 334:91; Lavelin et al. (2009) PLoS ONE 4:e8503). The best option would be a relatively simple assay that could be performed on living cells (Lavelin et al. (2009) PLoS ONE 4:e8503), preferably those from blood, and could be easily performed without the need for subcellular fractionation and PS isolation. Similarly, research on proteasomes would be advanced with a simple methodology that could be used to analyze PS activity under a variety of experimental conditions using live cells in cell culture or from blood. This would require a cell-permeable reagent that could specifically target PS components and produce an easily detectable signal with a minimum of equipment, preparation or expense. One such reagent has been described in the literature (Berkers et al. (2005) Nature Methods 2:382); however, this reagent, besides being relatively non-specific and very hydrophobic, does not distinguish between active and inactive proteasomes and is not commercially available.

SUMMARY OF THE INVENTION

In accordance with one aspect, the present invention provides a synthetic protease substrate of the formula:

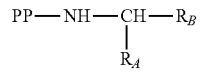

wherein PP represents a carboxy terminal-modified polypeptide, having a protease cleavage site, which undergoes cleavage upon exposure to protease activity and yields decomposition products including a compound comprising the $R_A$ moiety and a compound comprising the $R_B$ moiety, with one of such compounds being a reactive thiol derivative and the other being a reactive glyoxal derivative, and at least one of $R_A$ and $R_B$ moiety comprises a detectable reporter moiety. The polypeptide can be optionally protected with a protecting group.

In one embodiment of this invention, the PP moiety of the above formula is selected from the group consisting of a carboxy terminal-modified ubiquitin, a ubiquitin-like molecule, which is cleaved by a DUB. In another embodiment of this invention, the PP moiety is cleavable by a proteasome, wherein the polypeptide is a carboxy terminal-modified Pyz-Phe-Leu or Cbz-Leu-Leu-Leu. In the protease substrates of the instant invention, the cleavable site is in proximity to the modified glycine cleaving the $R_A$ and $R_B$ moieties.

In another embodiment of this invention, the $R_A$ moiety of the above formula has the formula —S—$R_a$ wherein $R_a$ is selected from the group of H, alkyl ($C_1$-$C_{10}$), aryl ($C_6$-$C_{14}$) L-Fl and L-Biot, wherein L represents a linker, -A-NH, in which A represents an alkylene moiety ($C_1$-$C_{10}$), a heteroalkylene moiety ($C_1$-$C_{10}$), an arylene moiety ($C_6$-$C_{14}$) or an aralkylene moiety ($C_7$-$C_{20}$), Fl represents a fluorophore and Biot is a biotinyl group; and the $R_B$ moiety has the formula —C(=O)—Rb, wherein Rb is selected from the group of hydroxy, alkoxy ($C_1$-$C_{10}$)-L' Fl and -L' Biot, wherein L' represents a linker, —NH—X—NH, in which X represents an alkylene ($C_1$-$C_{10}$), cycloalkylene ($C_3$-$C_{10}$), arylene ($C_6$-$C_{14}$), aralkylene ($C_7$-$C_{20}$) or heteroarylene moiety ($C_6$-$C_{10}$), Fl represents a fluorophore and Biot is a biotinyl group.

In yet another embodiment, at least one, and preferably both of the $R_A$ and $R_B$ moieties comprises a biotinyl group as the detectable reporter moiety.

According to another aspect of this invention, there is provided a method for determining protease activity, which comprises:

(a) exposing a substrate of the above-described formula to a protease under conditions suitable for cleavage of the $R_A$ moiety and $R_B$ moiety from the substrate; and (b) detecting the occurrence of cleavage from the substrate of at least one of the compound comprising the $R_A$ moiety and the compound comprising the $R_B$ moiety.

In one embodiment, the method of the invention further comprises the step of capturing at least one of the compounds yielded by the cleavage reaction on a capture device comprising a solid support on which a capture agent is immobilized, the capture agent having functional groups that form covalent or non-covalent chemical bonds with one of the reactive thiol derivative and/or the reactive glyoxal derivative. In this embodiment, the detecting step comprises detecting any reporter moiety present on the capture device, with the amount of reporter moiety detected being proportional to the concentration of active protease.

The above-described method may be performed according to a protocol in which the synthetic substrate is exposed to the protease in a vessel which also contains the capture device, or in which the substrate is exposed to the protease in a first vessel and is transferred to a second vessel which contains the capture device.

In a preferred embodiment, the protease is co-immobilized on the solid support with the capture agent or the protease itself functions as the capture agent.

According to another aspect of this invention, there is provided a method for determining protease activity in a plurality of cells by flow cytometry, which comprises:

(a) exposing a substrate of the above-described formula to a plurality of cells containing at least one protease under conditions suitable for cleavage of $R_A$ and $R_B$, wherein the $R_A$ and $R_B$ moieties comprise at least one fluorescent label;

(b) detecting by flow cytometry the cells which exhibit by fluorescence the occurrence of cleavage of at least one of said $R_A$ and $R_B$ moieties, and (c) calculating the number of cells of said plurality which demonstrate fluorescence, wherein fluorescence is indicative of protease activity.

In yet another embodiment of the invention, there is provided an assay kit comprising at least one synthetic substrate as described herein, and, as a positive control, at least one protease capable of cleaving the substrate and yielding the decomposition products necessary for practicing the assay; wherein the protease is a de-ubiquitylating enzyme (DUB) or a proteasome.

There are various embodiments of the assay kit of the invention. For example, the kit may include (i) multiple substrates, each substrate having the same polypeptide moiety and a different carboxy terminal-modifying moiety; (ii) multiple substrates, the polypeptide moieties of such substrates including at least two distinct polypeptide moieties, and each distinct polypeptide moiety is bound to the same carboxy terminal-modifying moiety which is different from the carboxy terminal-modifying moiety bound to any other distinct polypeptide moiety; and (iii) multiple substrates, the polypeptide moieties of such substrates including at least two distinct UB moieties, and all of the distinct polypeptide moieties are bound to the same carboxy terminal-modifying moiety.

One particularly notable advantage of the protease substrates described herein is the capability to transfer a detectable reporter moiety from the substrate to the enzyme itself, thereby making them suitable for use in multiplexed enzyme assays, e.g., on a catalytic microarray, or for labeling enzymes in situ in tissue slices or in cells using histocytochemical methods. Other advantages include the development of new reagents which demonstrate improved specificity and solubility. Since bortezomib contains a boronic acid active group which forms a covalent bond with a threonine present in the active site of one or more proteasomes, this group is replaced by the α-substituted glycine chemistry. The advantage of this approach is that the amide linkage between the bortezomib-derived moiety (Pyz-Phe-Leu) and the α-substituted glycine must be cleaved by the proteasome in order to liberate and activate the labeling reagent. The reagent will only produce a reactive label following cleavage by the proteasome thus ensuring that only active proteasomes will be labeled.

DETAILED DESCRIPTION OF THE INVENTION

Figure 1:
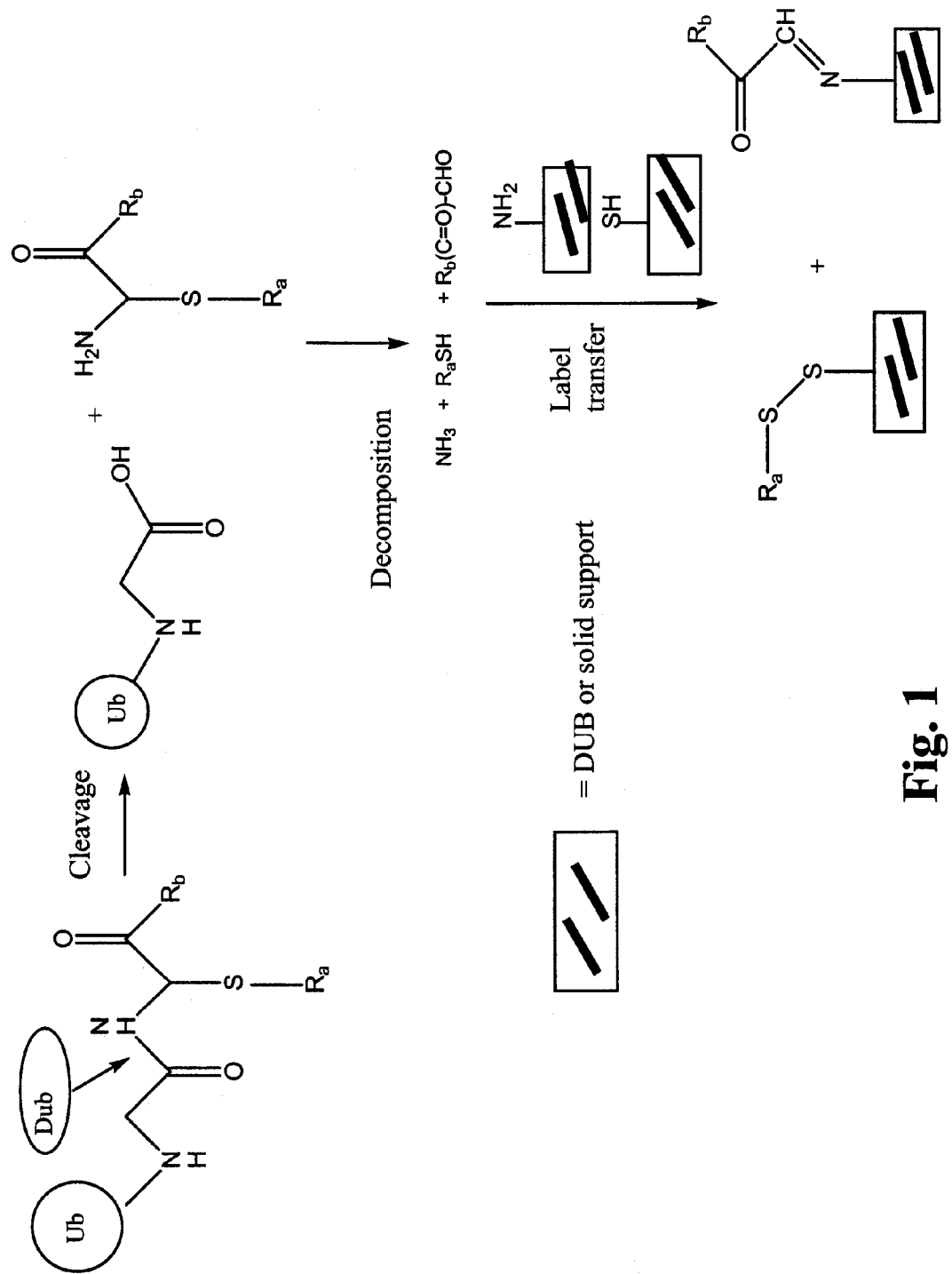
FIG. 1 is a schematic representation of a protease assay using a chemically modified polypeptide substrate in accordance with the invention. The rectangles in FIG. 1 represent DUB(s), a solid support or DUB(s) immobilized on a solid support.

The present invention provides materials and methods that are useful for the measurement of protease activity, particularly DUB activity. While the present invention will be described below with particular reference to the cleavage of chemically modified Ub and Ubls by DUBs, it will be apparent to those skilled in the art that the assay described herein can readily be adapted for the determination of other proteases of biomedical importance such as caspases, enzymes of the blood coagulation cascade, cathepsins, proteases of viral, bacterial or protozoal origin, matrix metalloproteases, or the like.

DEFINITIONS

The following definitions are provided to facilitate an understanding of the present invention.

The term "alkyl," as employed herein, includes both straight and branched chain hydrocarbons. An alkyl may contain 1 to 10, preferably 1 to 6 carbon atoms, and more preferably 1 to 4 carbon atoms. The hydrocarbon chain of the alkyl groups may be interrupted with oxygen, nitrogen, or sulfur. Examples of suitable alkyl groups include methyl, ethyl, propyl, isopropyl, butyl, t-butyl, isobutyl, pentyl, hexyl, isohexyl, heptyl, 4,4 dimethylpentyl, octyl, 2,2,4 trimethylpentyl, nonyl, decyl, the various branched chain isomers thereof, and the like. Similarly, the term "alkyl", or any variation thereof, used in combination form to name substituents such as alkoxy, or the like also refers to aliphatic hydrocarbon radicals of 1 to 10, 1 to 6 or 1 to 4 carbon atoms in length. Each alkyl group may optionally be substituted with 1 to 4 substituents which include, for example, halo, haloalkyl, alkoxy, alkylthio, hydroxyl, carboxyl, carboxylate, oxo, epoxy, alkyloxycarbonyl, alkylcarbonyloxy, amino, monoalkylamino, dialkylamino, carbamoyl, urea, alkylurea, aryl, amide, cyano, nitro and thiol.

The term "alkylene" refers to a divalent moiety that is derived from an alkane. The alkylene can be straight-chained, branched, cyclic ("cycloalkylene", e.g., cyclohexylene), or contain combinations thereof. The alkylene may have 1 to 10 carbon atoms, preferably 1 to 6 carbon atoms, or more preferably 1 to 4 carbon atoms. The alkylene may be substituted, e.g., with 1 to about 4 substituents, such as halo, haloalkyl (e.g., $CCl_3$ or $CF_3$), alkoxy, alkylthio, hydroxyl, carboxyl, oxo, epoxy, alkyloxycarbonyl, alkylcarbonyloxy, amino, monoalkylamino, dialkylamino, carbamoyl (e.g., $NH_2C(=O)$— or NHRC(=O)—, wherein R is alkyl), urea (—$NHCONH_2$), alkylurea, aryl, cyano, nitro, amide, carboxylate and thiol. The radical centers of the alkylene can be on the same carbon atom (i.e., an alkylidene), but are preferably on different carbon atoms. "Heteroalkylene" refers to an alkylene that includes at least one, and preferably from 1 to about 4 sulfur, oxygen, or nitrogen heteroatoms substituted for a carbon in the alkane.

The term "aryl," as employed herein, refers to a cyclic aromatic group comprising one to five rings, preferably one to three rings (e.g., 6 to 14 carbons), and more preferably one or two rings (e.g., 6 to 10 carbons). The rings may be connected, fused, or include combinations thereof and at least one ring is aromatic. Examples of aryl groups include, without limitation, phenyl, naphthyl, such as 1-naphthyl and 2-naphthyl, indolyl, and pyridyl, such as 3-pyridyl and 4-pyridyl. Aryl groups may be optionally substituted through available carbon atoms with 1 to about 4 substituent groups. Exemplary substituents may include, but are not limited to, alkyl, halo, haloalkyl, alkoxy, alkylthio, hydroxyl, carboxyl, carboxylate, oxo, epoxy, alkyloxycarbonyl, alkylcarbonyloxy, amino, monoalkylamino, dialkylamino, carbamoyl, urea, alkylurea, amide, cyano, nitro, and thiol. The aromatic groups may be heteroaryl. "Heteroaryl" refers to an optionally substituted aromatic ring system that includes at least one, and preferably from 1 to about 4 sulfur, oxygen, or nitrogen heteroatom ring members.

The term "arylene" refers to a divalent moiety derived from an aryl group. The group has one to five rings that are connected, fused, or includes combinations thereof wherein at least one ring is aromatic. For example, the arylene group can be phenylene, biphenylene or napthylene. "Heteroarylene" refers to an arylene moiety of 6 to 10 ring atoms that includes at least one, and preferably from 1 to about 4 sulfur, oxygen, or nitrogen heteroatoms substituted for a carbon in the aromatic ring. The term "aralkylene", as used herein, is a combined form of "arylene" and "alkylene", as defined above, and includes, e.g., benzylene. The arylene heteroarylene or aralkylene moiety can optionally be substituted in the same manner described above with respect to the "aryl" and "alkyl" groups, as the case may be.

The terms "halogen," "halo," and "halide" refer to chlorine, bromine, fluorine or iodine.

The term "polypeptide moiety", as used herein, refers to any of various natural or synthetic compounds comprising two or more amino acid molecules, which may be the same or different, and which are linked by the carboxyl group of one amino acid to the amino group of another amino acid. The polypeptide moiety may be derived from an oligopeptide, e.g., di-, tri-, or tetrapeptides, or from a longer amino acid chain of 100 amino amino acids or more, including proteins. The polypeptide moiety may optionally be protected, if desired, by a suitable protecting group as further explained below.

The term "protecting group", as used herein, refers to a grouping of atoms that when attached to a reactive functional group in a molecule masks, reduces, or prevents reactivity of the functional group. Examples of suitable protecting groups can be found in Kocienski, P. J., "Protecting Groups", (Thieme, 1994) and Green et al., "Protecting Groups in Organic Chemistry", (Wiley, $2^{nd}$ ed. 1991). Representative amino protecting groups include, but are not limited to formyl, acetyl, trifluoroacetyl, benzyl, benzyloxycarbamoyl (Cbz), tert-butoxycarbamoyl (Boc), trimethylsilyl (TMS), 2-trimethylsilyl-ethanesulfonyl (SES), trityl, and substituted trityl groups, allyloxy carbonyl, 9-fluorenylmethyloxycarbonyl (Fmoc), nitro-veratryloxy carbonyl (NVOC) and the like. Representative hydroxyl protecting groups include, but are not limited to, acyl and alkyl groups, such as benzyl, and trityl ethers as well as alkyl ethers, tetrahydropyranyl ethers, trialkylsilylethers, and allyl ethers.

The term "substantially pure" refers to a preparation comprising at least 50-60% by weight of a given material (e.g., nucleic acid, oligonucleotide, protein, etc.). More preferably, the preparation comprises at least 75% by weight, and most preferably 90-95% by weight of the given compound. Purity is measured by methods appropriate for the given compound (e.g. chromatographic methods, agarose or polyacrylamide gel electrophoresis, HPLC analysis, and the like).

It should be appreciated that the compounds represented may have one or more asymmetric centers and thus exist as stereoisomers, including diastereomers, with stereocenters named according to the Cahn-Ingold-Prelog system (R/S designation of stereocenters). Although the structural formulas set forth above are represented without regard to stereochemistry, it is intended to include all possible stereoisomers, which may be diastereomeric mixtures, as well as resolved, substantially pure optically active and inactive forms, and pharmaceutically acceptable salts thereof.

Stereoisomers of the compounds used in the practice of this invention can be selectively synthesized or separated into pure, optically-active or inactive form using conventional procedures known to those skilled in the art of organic synthesis. For example, mixtures of stereoisomers may be separated by standard techniques including, but not limited to, resolution of diastereomeric forms, normal, reverse-phase, and chiral chromatography, preferential salt formation, recrystallization, and the like, or by asymmetric synthesis either from enantiomerically or diastereomerically pure starting materials or by deliberate synthesis of target enantiomers or diastereomers. All of the various isomeric forms of the proteasome substrates represented are within the scope of this invention.

The phrase "enantiomeric excess" or "ee" is a measure, for a given sample, of the excess of one enantiomer over a racemic sample of a chiral compound and is expressed as a percentage. Enantiomeric excess is defined as $100*(er-1)/(er+1)$, where "er" is the ratio of the more abundant enantiomer to the less abundant enantiomer.

The phrase "diastereomeric excess" or "de" is a measure, for a given sample, of the excess of one diastereomer over a sample having equal amounts of diastereomers and is expressed as a percentage. Diastereomeric excess is defined as $100*(dr-1)/(dr+1)$, where "dr" is the ratio of a more abundant diastereomer to a less abundant diastereomer. The term does not apply if more than two diastereomers are present in the sample.

The term "isolated protein" or "isolated and purified protein" is sometimes used herein. This term refers primarily to a protein produced by expression of an isolated nucleic acid molecule of the invention. Alternatively, this term may refer to a protein that has been sufficiently separated from other proteins with which it would naturally be associated, so as to exist in "substantially pure" form. "Isolated" is not meant to exclude artificial or synthetic mixtures with other compounds or materials, or the presence of impurities that do not interfere with the fundamental activity, and that may be present, for example, due to incomplete purification, addition of stabilizers, or compounding into, for example, immunogenic preparations or pharmaceutically acceptable preparations.

As used herein, the term "solid support" refers to any solid or stationary material to which reagents such as capture agents, proteases, antibodies, antigens, or the like, can be immobilized or cleavably attached. Examples of solid supports include, without limitation, microtiter plates (or dish), microscope (e.g. glass) slides, coverslips, beads, cell culture flasks, chips (for example, silica-based, glass, or gold chip), membranes, particles (typically solid; for example, agarose, sepharose, polystyrene or magnetic beads), columns (or column materials), and test tubes. Typically, the solid supports are water insoluble.

The term "kit" refers to a combination of reagents and other materials.

As used herein, an "instructional material" includes a publication, a recording, a diagram, or any other medium of expression which can be used to communicate the manner in which the substrates described herein are used in practicing the assay of the invention.

In accordance with the present invention, α-substituted glycine-modified substrates have been developed for use in the assay method described herein. One such array, involving the use of a substrate having an isopeptidase (DUB) cleavage site is illustrated in FIG. 1. As exemplified below, the substrates are obtainable by chemically coupling substituted dipeptides, as described herein, to the carboxyl terminus of des-Gly-Ub, i.e., native Ub from which the carboxyl-terminal glycine residue has been removed, which is referred to herein as UbΔG76. These substrates will be suitable for use in the assay of FIG. 1 to measure the activity of immobilized DUBs in a multiplex environment and for tissue staining. Compared to conventional assays, in which enzymes are tested one at a time, a multiplex assay provides a distinct practical advantage for screening enzyme inhibitors or activators, especially in the case of large numbers of related enzymes, such as DUBs.

Figure 2:
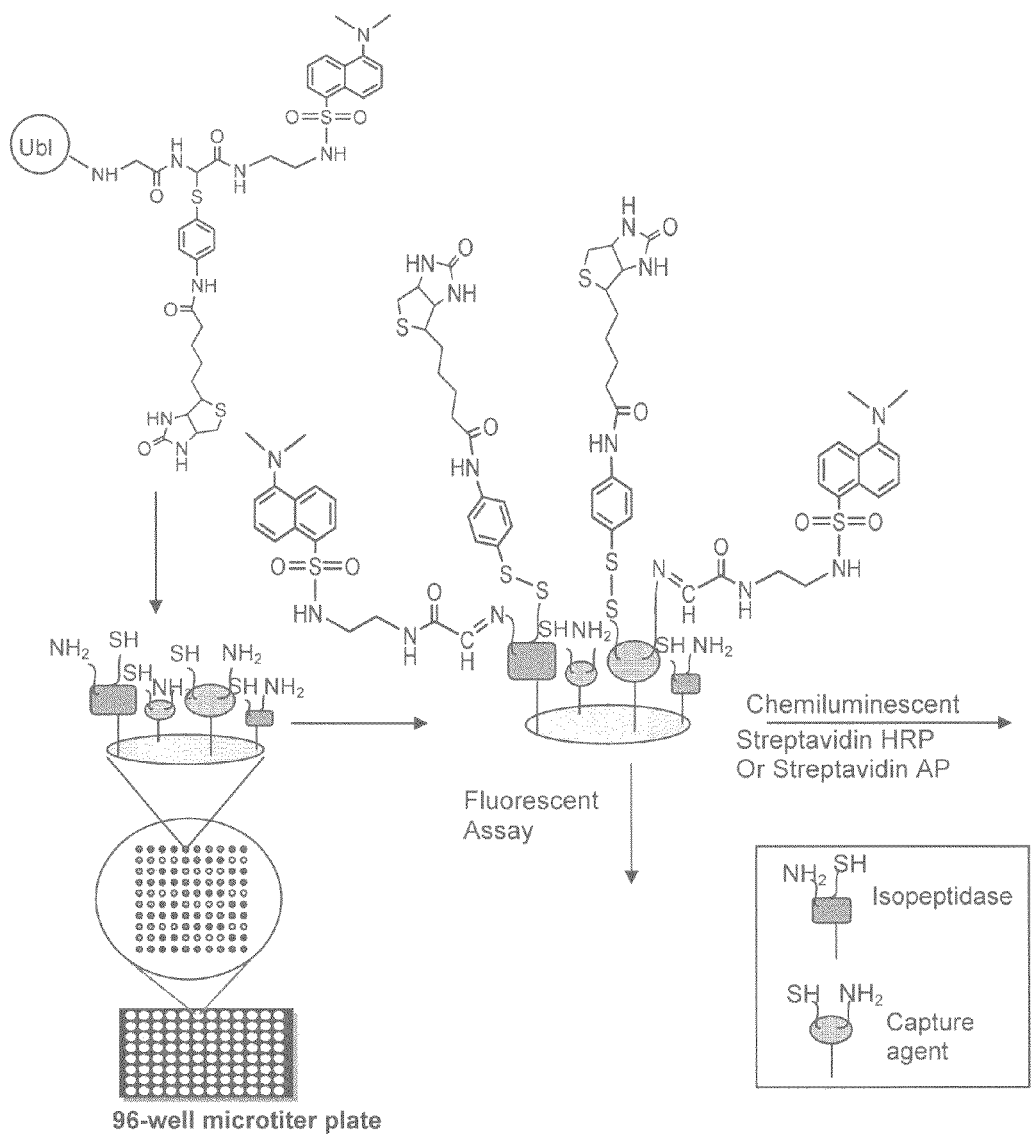
FIG. 2 is a schematic representation of a protease assay, in microarray format, using a chemically modified UB substrate and biotin as the detectable reporter moiety, with fluorescent, chemiluminescent, and colorimetric detection of the detectable reporter moiety, in accordance with the invention. The microarray format is an illustrative example of such as assay.

Upon cleavage of the amide bond immediately adjacent to the α-substituted glycine (the scissile bond) by a DUB, the α-substituted glycine undergoes decomposition leading to the formation of a thiol derivative, a glyoxal derivative and ammonia, as can be seen in FIG. 1 (Kingsbury, Boehm et al. (1984) Proc. Natl. Acad. Sci. USA, 81, 4573; Hwang, Kingsbury et al., (1986) Anal. Biochem., 154: 552; Kingsbury and Boehm (1986) Int. J. Peptide Protein Res., 27: 659; Brown, Kingsbury et al. (1987) Anal. Biochem., 161: 219). The thiol derivative can then be captured through the formation of a disulfide bond with cysteine residues in the DUB protein, while the glyoxal can be captured via the formation of a Schiff base with primary amines within the DUB protein, e.g., the s-amino group of Lys. The Schiff base can be subsequently reduced to a more stable amide bond, e.g., in the presence of $NaBH_3CN$. Alternatively, an amino or thiol containing substrate (e.g., polylysine, polycysteine, or a protein, such as bovine serum albumin (BSA), hen ovalbumin or the like, can be co-immobilized with the protease to serve as a capture agent (FIG. 2). Upon covalent capture of the decomposition products, unbound reagents can be washed away. Because Ub and Ubls are free of cysteines, and aldehyde functionalities are not found in proteins, there is no concern that other reactive species will compete with the products produced from the cleavage reaction for capture by the capture agent. Depending on their identity, the captured products can then be analyzed quantitatively or qualitatively. A fluorophore- or biotin-containing substituent can be used effectively as the detectable reporter moiety of the thiol derivative or glyoxal derivative. Localization is achievable either by direct fluorescence of the fluorophore or following binding of a labeled-avidin conjugate to the biotin moieties. A variety of sensitive, commercially available and well-characterized fluorescence, chemiluminescence and colorimetric assays that are based on this binding event can be adapted for the activity measurement. Thus, the diverse potential of these assays eliminates the need for any specialized analytical instrumentation for the catalytic activity measurement. A fluorogenic, luminogenic, or chromogenic moiety may be selected such that only after the cleavage and capture steps does the moiety become colored or fluorescent. The amount of immobilized, detectable reporter moiety is proportional to the amount of active DUB. Imaging agents such as chromophores, colloidal gold, or quantum dots, to name a few, could be incorporated into the thiol derivative and/or the glyoxal derivative, if desired, using procedures familiar to those skilled in the art. Since the DUB cleavage products are trapped and presented on a surface, the assay is ideal for detecting enzymes in a microarray format or in histo- or cytochemical studies.

Representative examples of α-substituted glycines used to produce the synthetic protease substrate of the invention are shown in Table 4. A suitable synthesis for the Example 1-3 compounds is set forth below in Reaction Scheme 1.

TABLE 4

Structure of α-substituted glycines used to modify Ub/Ubls

| Ex. No. | Compound | R1 |
|---|---|---|
| 1 | [structure shown] | Ph |

TABLE 4-continued
Structure of α-substituted glycines used to modify Ub/Ubls
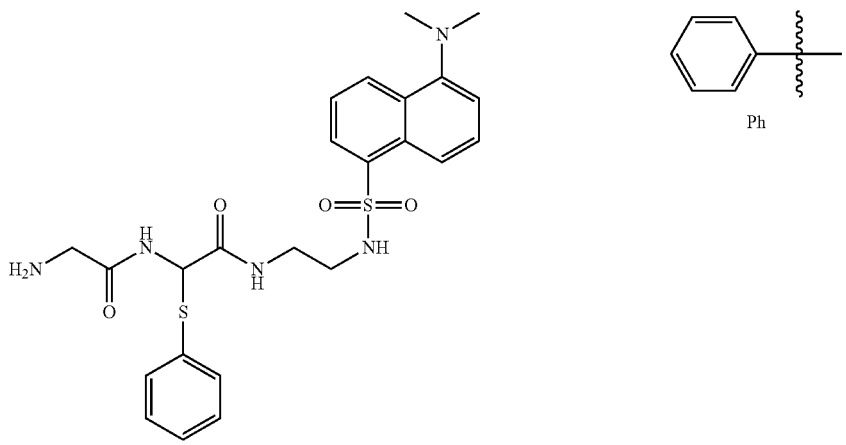
2
3
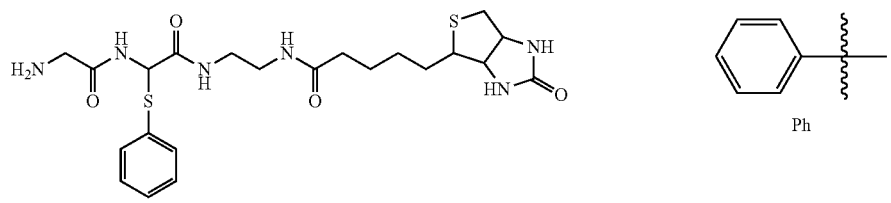
4
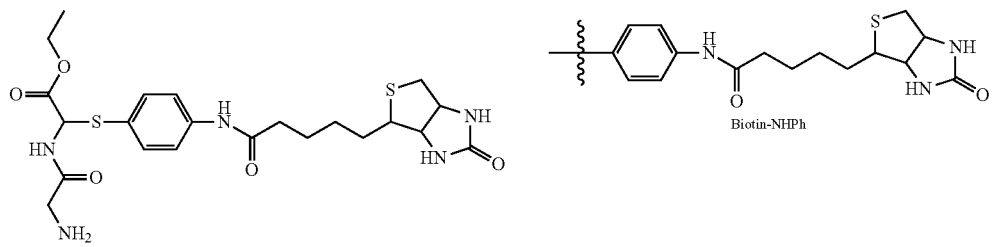
Biotin-NHPh
| Ex. No. | R2 |
|---|---|
| 1 | 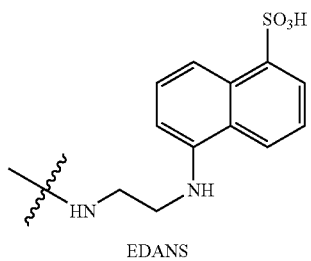 [SMILES: *NCCNc1cccc2c(S(=O)(=O)O)cccc12] EDANS |
| 2 | 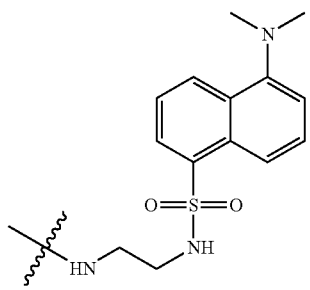 Dansylamide |

TABLE 4-continued

Structure of α-substituted glycines used to modify Ub/Ubls

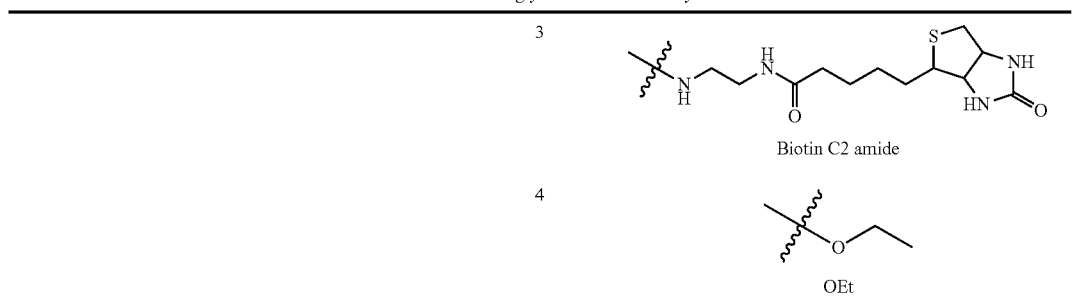

3  Biotin C2 amide

4  OEt

Briefly, condensation of Cbz-glycinamide 1 with glyoxylic acid monohydrate in acetone gives the corresponding α-hydroxy derivative 2. Treatment of 2 with thiophenol in AcOH and with concentrated $H_2SO_4$ gives thioether-acid 3, which is coupled to the amine group of 4, 5 or 6 to produce Cbz-protected derivatives 7, 8 or 9. Removal of the protecting group with HBr/AcOH affords the desired α-substituted glycines.

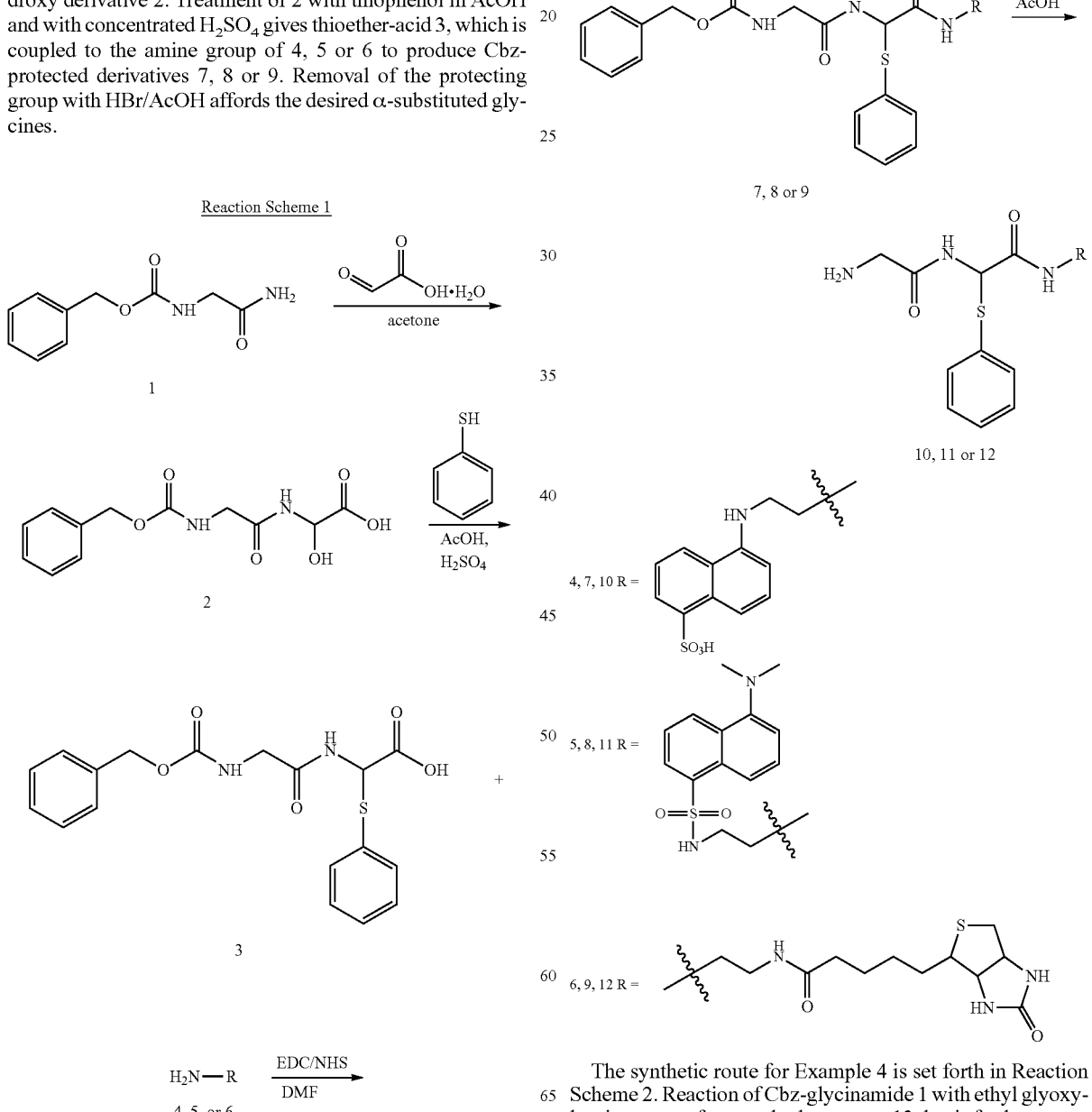

The synthetic route for Example 4 is set forth in Reaction Scheme 2. Reaction of Cbz-glycinamide 1 with ethyl glyoxylate in acetone forms α-hydroxy ester 13 that is further acetylated to produce 14. The biotinylated linker 17 is synthesized in two steps, involving reaction of commercially available NHS-biotin 15 with 4,4'-Dithiodianiline to produce 16, and reduction of the disulfide bond with zinc. Compound 17 thus produced displaces the acetate in compound 14 to yield Cbz-protected derivative 18. Removal of the protecting group with HBr/AcOH afforded the desired α-substituted glycine 19.
Reaction Scheme 2
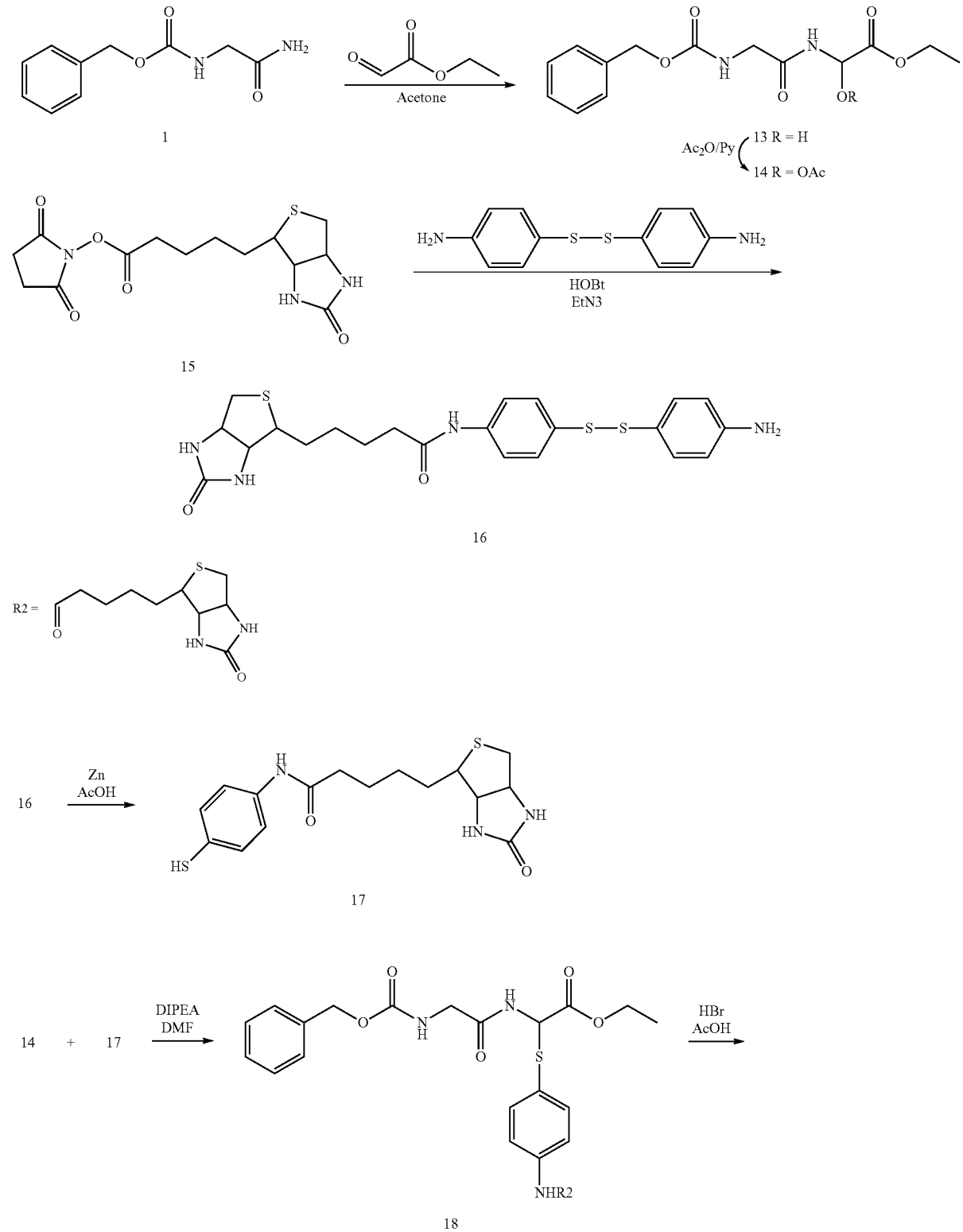

-continued

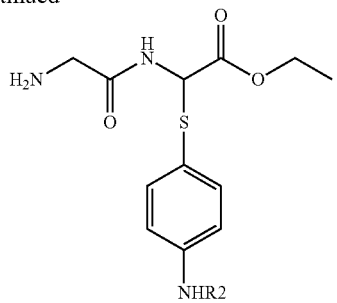

19

One embodiment of the enzyme substrates within the scope of this invention is chemically-modified Ub. In preparing this substrate, UbΔG76 was expressed in *E. coli* as a fusion protein with an intein and chitin binding domains. I. Cottingham et al., *Nature Biotechnology* 19, 974-977 (2001). Purification and transthioesterification was performed on a chitin affinity column using sodium β-mercaptoethanesulfonic acid (MESNA) to cleave the protein. The resulting UbΔG76-MESNA thioester was reacted with the α-substituted glycine, obtained using Reaction Scheme 1 or 2, above to produce the desired Ub-substrates according to the following scheme:

In another embodiment of the invention, a proteasome substrate is synthesized utilizing bortezomib or Cbz-Leu-Leu-Leu-AMC fragments rather than Ub or a ubiquitin-like protein. The boronic acid substituent of bortezomib or the AMC reporter of the proteasome specific AMC-polypeptide are replaced with α-substituted glycine chemistry. The structure of bortezomib was selected as a starting point since it has already been designed to be highly specific for proteasomes and to be membrane permeable. Since bortezomib contains a boronic acid active group which forms a covalent bond with a threonine in the active site of one or more of the proteasome

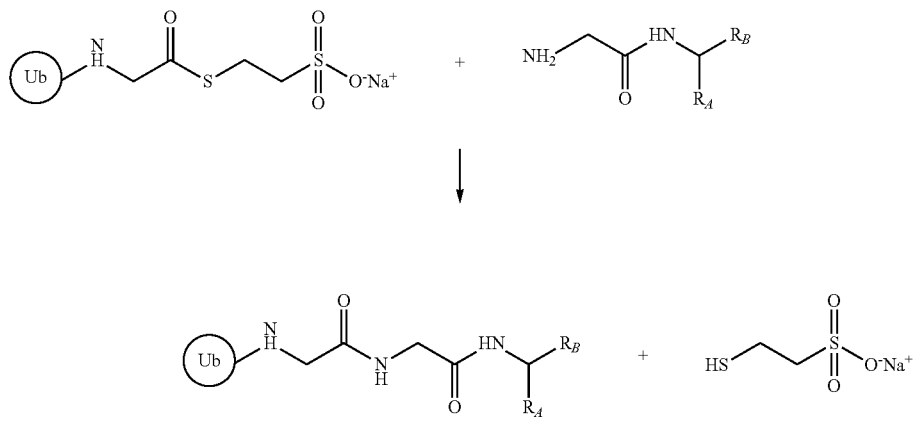

Reaction Scheme for Synthesis of DUBs Substrates

Since not all DUBs recognize a given substrate to the same extent, synthesis of a substrate library will allow for the selection of the best substrate for a given DUB.

To assure that the immobilized BSA, if used, or NaCNBH$_3$ does not affect the DUB cleavage, control experiments may be carried out. To assess the background signal, reactions may also be carried out in the absence of DUBs as a negative control. In order to compare the sensitivity of the assay of the invention to that of Ubl-AMC and Lanthascreen TR assay reagents, control assays may be carried out using these reagents under the same conditions. A signal-to-noise ratio >1 may be considered as an activity signal.

proteases, this group was replaced with the α-substituted glycine chemistry described hereinabove.

The design of the proteasome substrates is outlined in Scheme 3. Upon cleavage of the amide bond between the α-substituted glycine and Bortezomib dipeptide (Pyrazinoic acid (Pyz)-Phe-Leu), the α-substituted glycine will spontaneously undergo decomposition leading to the formation of Pyz-Phe-Leu, ammonia, thiophenol and a substituted aldehyde (Scheme 3). The aldehyde carries either a dansyl group or a BODIPY group, which will be transferred, covalently, to the proteasome by reductive amination and enable facile isolation and identification.

Scheme 3. Proteasome substrates design is based on the incorporation of α-substituted glycine.
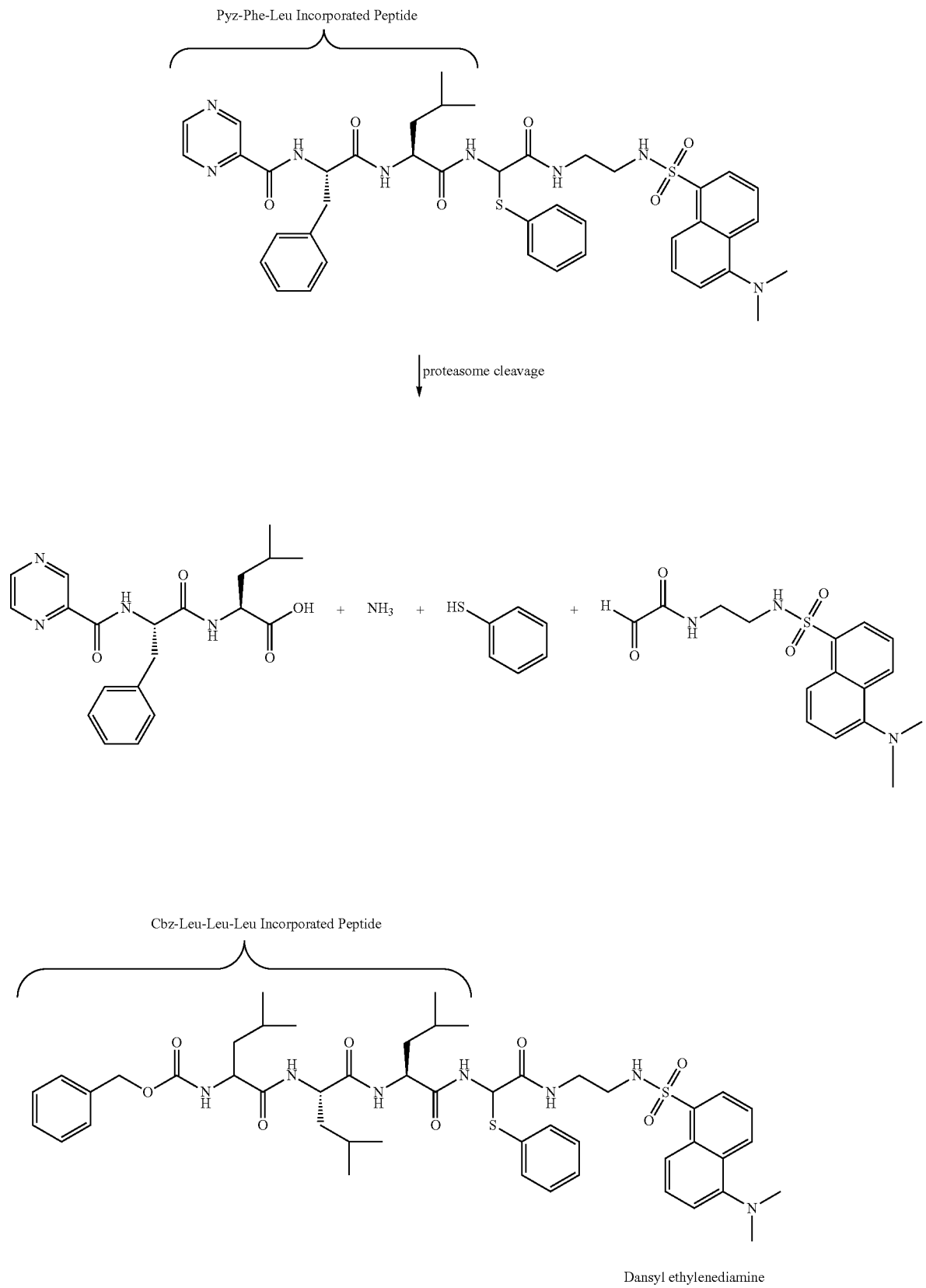
Dansyl ethylenediamine Cbz-Leu-Leu-Leu Incorporated Peptide

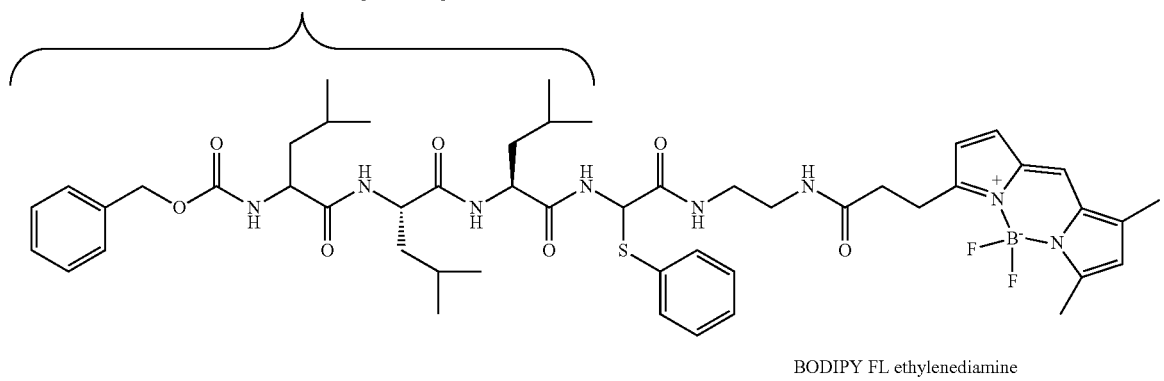

BODIPY FL ethylenediamine

To avoid complications arising from Fmoc-deprotection of α-substituted glycine on 2-Cl-trityl resin, dipeptide 22 is prepared in solution phase for resin attachment (Scheme 4). The Fmoc-Leu-NH$_2$ (20) is reacted with the glyoxylic acid to form the α-hydroxyamide diastereomers 21. The dipeptide 22 is formed after treatment with thiophenol and acid.

Scheme 4. Synthesis of α-substituted glycine dipeptide 22.

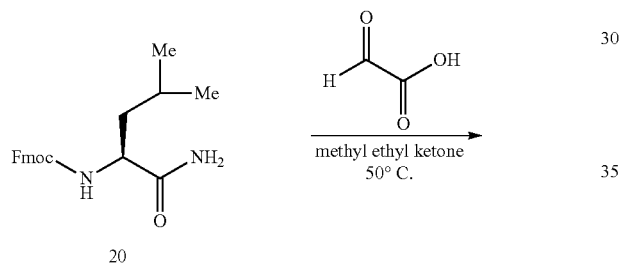

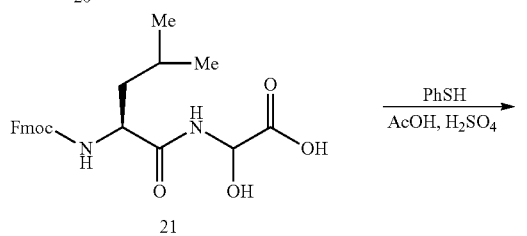

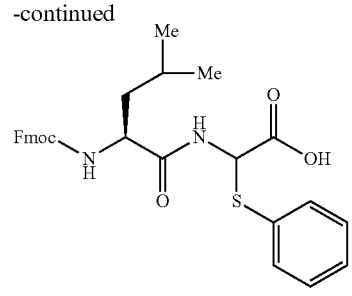

22

Dipeptide 22 is loaded onto 2-chlorotrityl resin under standard conditions. Subsequent elongation to the tripeptide 25 is carried out using standard Fmoc-based peptide synthesis (Scheme 5). Resin cleavage with acid yields peptide 26, which is coupled to dansyl ethylenediamine to afford the Pyz-Phe-Leu Proteasome Substrate bearing a dansyl fluorophore from Scheme 3. Cbz-Leu-Leu-Leu Proteasome Substrates bearing the BODIPY and dansyl fluorophores from Scheme 3 are prepared in the same manner (Scheme 6).

Scheme 5. Synthesis of the Pyz-Phe-Leu proteasome substrate bearing a dansyl fluorophore from Scheme 3 by solid phase synthesis.

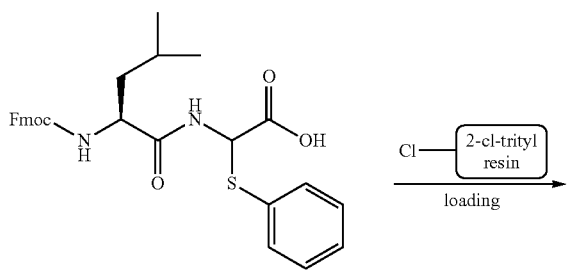

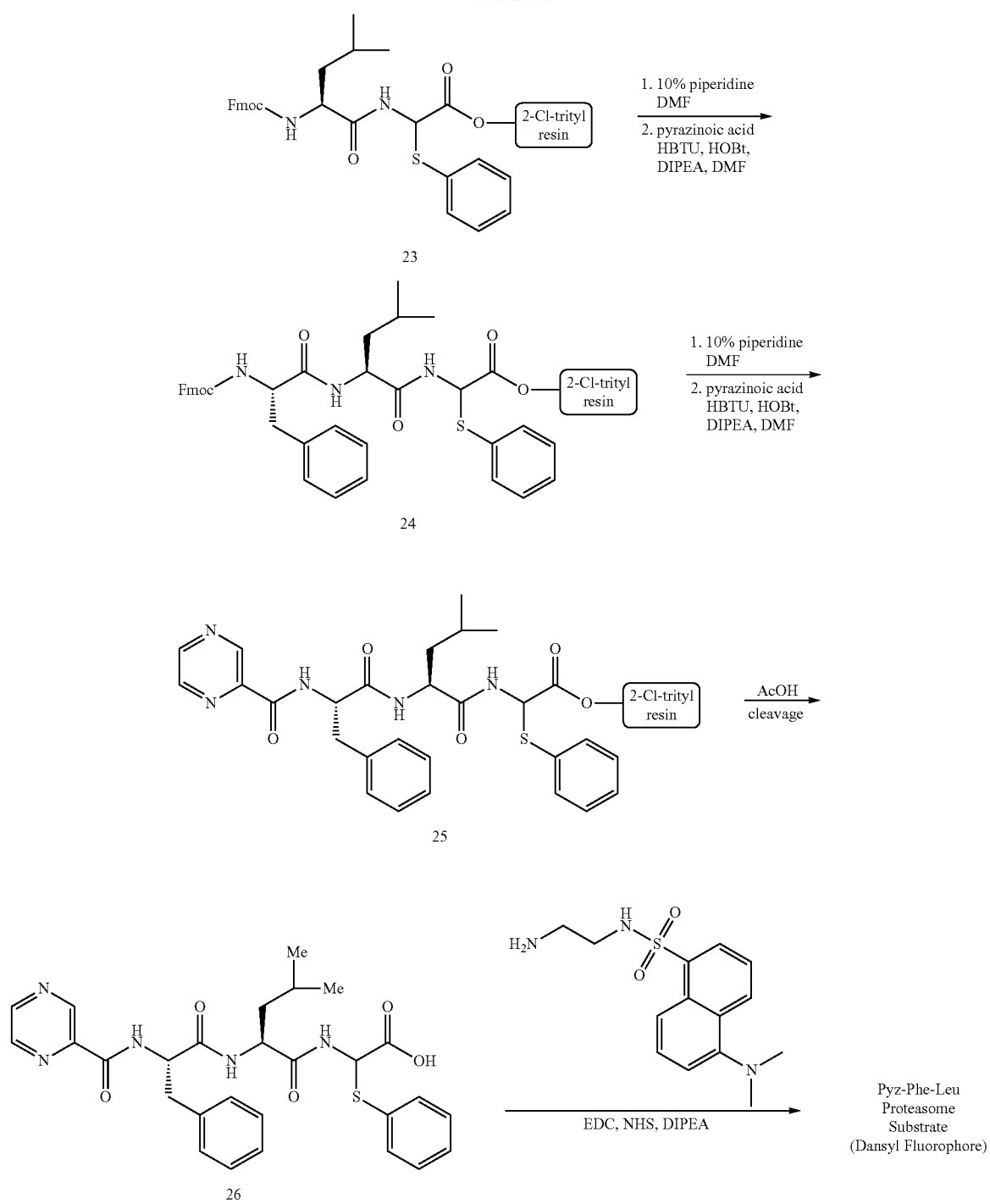
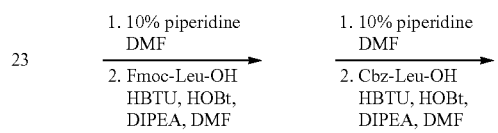
Scheme 6. Synthesis of the Cbz-Leu-Leu-Leu proteasome substrate bearing a dansyl fluorophore from Scheme 3 by solid phase synthesis.

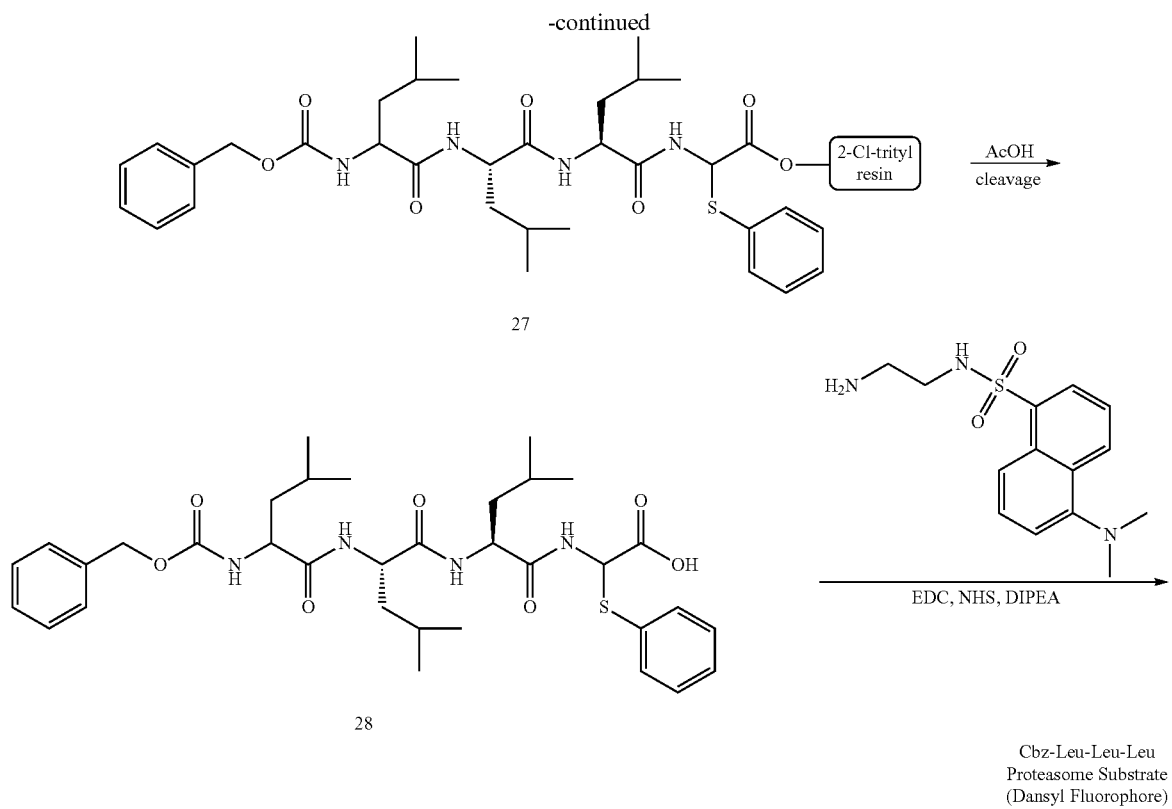

Cbz-Leu-Leu-Leu Proteasome Substrate (Dansyl Fluorophore)

Performance of the assay described herein can be facilitated by providing necessary materials in kit form. Such a kit may comprise at least one synthetic substrate as described herein, and, as a positive control, at least one de-ubiquitylating enzyme (DUB) or a proteasome capable of cleaving said substrate and yielding said decomposition products.

The contents of the kit may vary depending on the determination(s) sought to be made. Kits may include two, three, four or more aliquots of a substrate as described herein, comprising Ub, a single Ubl, Pyz-Phe-Leu, or a Cbz-Leu-Leu-Leu, each with a different carboxy-terminal modifying moiety. Alternatively, a combination of Ub and Ubl, e.g., SUMO (or multiple Ubls) may be provided, each with a carboxy terminal-modifying moiety, which may be the same or different. The kit may also include an assay device which comprises a solid support having a multiplicity of different DUBs or proteasomes immobilized on a surface thereof, thereby enabling the assay to be performed in a multiplex environment.

There may also be included in the kit one or more vessels usable for mixing or dispensing assay reagents, as well as instructional material for proper performance of the assay.

The assay of the present invention may also be used to profile biological fluids such as cerebrospinal fluids (CSFs) for the presence of DUBs. CSFs are a rich source of neurological disease markers and are well analyzed for a variety of neurological disorders. DUBs may play a key role in many of these disorders and could thus be important biomarkers. Because of the difficulty in obtaining large amounts of CSF a cerebrospinal fluid reverse array could be used wherein very small samples of CSF are spotted on a chip and assayed for the isopeptidase activity. The use of a biotin or biotin like ligand enables one to amplify the signal and increase the sensitivity of the assay and allow for high throughput catalytic activity analysis using less than a microliter of sample. The CSF reverse array is an excellent diagnostics/prognostics tool as it can be used for population profiling and biomarker discovery. Indeed, the over- or under-expression of DUBs in the CSF may indicate the onset or presence of disease. The DUBs can then be identified and evaluated as potential biomarkers. Once a DUB is identified as a biomarker, the best assay reagent for this particular DUB from the library can be used for screening and to identify inhibitors. A comprehensive microarray analysis of DUB proteins found in the CSF of control and NDD patients will identify novel DUBs that are affected in NDDs and will provide novel avenues for drug discovery. DUB activity can also be measured in brain and spine tissue samples obtained from patients with neurological disorders.

Flow cytometry is a method of analyzing cell subpopulations, in a moving liquid stream, using automated equipment. It is widely used in medical labs and in biomedical and biochemical research, and it is discussed in various books and articles such as Haynes and Melamed et al. (Haynes, Cytometry Supplement, (1988) 3:7-17; Melamed et al., eds., Flow Cytometry and Sorting, 2nd edition, Wiley and Liss, New York, 1990) and in journals such as Cytometry and the American Journal of Clinical Pathology. Flow cytometry is unique, as compared to other diagnostic techniques, in its capability to perform simultaneous multiparameter analysis and to separate (or sort) unique cell sub-populations from heterogeneous cell mixtures. Cellular analysis generally includes visual inspection via light or fluorescent light microscopy and can further include automated analysis by means of image analysis and flow cytometry. Cells, containing proteases, are exposed to a fluorescently labeled protease substrate and suspended in solution. The cells are then analyzed via flow cytometry using occurrence of cleavage of the protease substrate in the manner described above, resulting in measurable fluorescence, to identify protease activity in a subset of cells among a larger cell population. The quantity of cells demonstrating protease activity, in a homogenous or heterogeneous sample of cells, can then be calculated.

The following examples describe the invention in further detail. These examples are provided for illustrative purposes only and should in no way be construed as limiting the invention. The substrate synthesis provided in the examples are described with reference to Reaction Schemes 1 and 2, above.

Example 1

Synthesis and characterization of 5-(2-(2-(2-aminoacetamido)-2 (phenylthio)acetamido)ethylamino) naphthalene-1-sulfonic acid (10)

A mixture of Cbz-Gly-NH$_2$ (1) (1.0 g, 4.8 mmol) and glyoxylic acid monohydrate (0.56 g, 6 mmol) in acetone (25 mL) was heated at 50° C. for 72 h. The acetone was evaporated under reduced pressure and the residue was purified by RP-HPLC to give 0.53 g (39%) of product (2). ESI-MS m/z 283.2 (M+1)$^+$ A solution of 2 (0.75 g, 2.7 mmol) in acetic acid (17 mL) was cooled in ice and thiophenol (0.6 mL, 5.4 mmol) was added followed by 0.9 mL of sulfuric acid. After stirring at room temperature for two days, the mixture was poured onto ice and extracted with ethyl acetate. The ethyl acetate solution was washed with saturated sodium bicarbonate, with water and dried over MgSO$_4$. The ethyl acetate was evaporated under reduced pressure and the residue was purified by RP-HPLC to give 0.56 g (56%) of product (3). ESI-MS m/z 375.4 (M+1)$^+$ To a solution of 3 (0.1 g, 0.26 mmol) in dry DMF (40 mL) were added N,N-Diisopropylethylamine (DIPEA) (0.030 mL), 4[5-((2-Aminoethyl)amino)naphthalene-1-sulfonic acid] (EDANS) (0.084 g, 0.32 mmol), N-(3-Dimethylaminopropyl)-N'-ethylcarbodiimide hydrochloride (EDC) (0.062 g, 0.32 mmol) and N-Hydroxysuccinimide (NHS) (0.036 g, 0.32 mmol). After stirring at room temperature overnight, the solvent was removed under reduced pressure and the residue was dissolved in DMSO and purified by RP-HPLC to give 0.092 g (55%) of product (7).

Removal of the Z group was accomplished in quantitative yield by adding a solution of 30% HBr in AcOH (2 mL) to compound 7 (0.072 g, 0.12 mmol) and stirring for 30 min in an ice bath. The mixture was evaporated under reduced pressure and the residue was dissolved in DMSO and purified by RP-HPLC to give the desired product 10. ESI-MS m/z 489.53 (M+1)$^+$.

Example 2

Synthesis and Characterization of 2-(2-aminoacetamido)-N-(2-(5-(dimethylamino)naphthalene-1-sulfonamido)ethyl-2-(phenylthio)acetamide (11)

To a solution of 3 (0.060 g, 0.16 mmol) in dry DMF (20 mL) were added DIPEA (0.010 mL), Dansyl ethylendiamine (0.065 g, 0.22 mmol), EDC (0.036 g, 0.19 mmol) and NHS (0.022 g, 0.19 mmol). After stirring at room temperature overnight, the solvent was removed under reduced pressure and the residue was dissolved in DMSO and purified by RP-HPLC to give 0.083 g (80%) of product (8). ESI-MS m/z 650.69 (M+1)$^+$.

Removal of the Z group was accomplished in quantitative yield as described before. The mixture was evaporated under reduced pressure and the residue was dissolved in DMSO and purified by RP-HPLC to give the desired product 11. ESI-MS m/z 516.55 (M+1)$^+$.

Example 3

Synthesis and Characterization of N-(2-(2-(2-aminoacetamido)-2-(phenylthio)acetamido)ethyl-5-(2-oxohexahydro-1H thieno[3,4-d]imidazol-4-yl)pentanamide (12)

To a solution of 3 (0.10 g, 0.27 mmol) in dry DMF (2 mL) were added DIPEA (0.053 mL), Biotin ethylenediamine, hydrobromide (0.118 g, 0.32 mmol), EDC (0.061 g, 0.32 mmol) and NHS (0.037 g, 0.32 mmol). After stirring at room temperature for 3 days, the solvent was removed under reduced pressure and the residue was dissolved in DMSO and purified by RP-HPLC to give 0.085 g (49%) of product (9). ESI-MS m/z 643.17 (M+1)$^+$.

Removal of the Z group was accomplished in quantitative yield as described before. The mixture was evaporated under reduced pressure and the residue was dissolved in MeOH and filtered through silica to give the desired product 12. ESI-MS m/z 509.11 (M+1)$^+$.

Example 4

Ethyl 2-(2-(aminoacetamido)-2-(4-(5-(2-oxohexahydro-1H-thieno[3,4-d]imidazol-4-yl)pentanamido) phenylthio)acetate (19)

A mixture of Cbz-Gly-NH$_2$ (1) (2.0 g, 10 mmol) and 50% ethyl 2-oxoacetate in toluene (1.04 g, 10 mmol) and acetone as solvent (20 mL) was stirred at 45° C. for 16 h. At this time, the solvent was removed under reduced pressure to give compound 13. ESI-MS m/z 311.08 (M+1)$^+$. The crude product was used for the next step without further purification.

Compound 13 was dissolved in acetic anhydride (2.5 mL) and pyridine (5 mL). The resulting mixture was stirred at room temperature for 3 h. The solvent was removed under reduced pressure and the residue was dissolved in ethyl acetate, washed with 1M HCl, 5% NaHCO$_3$, saturated NaCl and dried (MgSO$_4$). The ethyl acetate was evaporated under reduced pressure and the residue was purified by RP-HPLC to give 1.59 g (47%) of product (14). ESI-MS m/z 375.4 (M+Na)$^+$ To a solution of 4,4'-disulfanediyldianiline (0.2 g, 0.81 mmol) in dry DMF (40 mL) were added biotin-NHS 15 (0.3 g, 0.88 mmol), hydroxybenzotriazole (HOBt—0.108 g, 0.80 mmol) and Et$_3$N (0.080 mL). After stirring at 50° C. for 4 d, the solvent was removed under reduced pressure and the residue was dissolved in DMSO and purified by RP-HPLC to give 0.225 g (59%) of product (16). ESI-MS m/z 475.18 (M+H)$^+$.

To a solution of 16 (0.040 g, 0.084 mmol) in AcOH (1 mL), Zn (0.038 g, 0.58 mmol) was added and the mixture was stirred at 60° C. for 12 h. The reaction mixture was filtered to and the solution was concentrated under reduced pressure to give compound 17 (30 mg), which was used for the next reaction without further purification. ESI-MS m/z 352.09 (M+H)$^+$.

To a solution of compounds 14 (0.030 g, 0.085 mmol) and 17 (0.030 g, 0.085 mmol) in dry DMF (2 mL) N,N-diisopropylethylamine (DIPEA-20 µL) was added and the reaction was stirred for 24 h at room temperature. The solvent was removed under reduced pressure to give compound 18. ESI-MS m/z 644.11 (M+1)$^+$. The crude product was deprotected adding a solution of 30% HBr in AcOH (1.5 mL) and stirring for 1 h in an ice bath. The mixture was evaporated and purified by RP-HPLC to give product 19 (0.012 g, 28%). ESI-MS m/z 510.14 (M+H)$^+$.

Example 5

Synthesis of 2-((S)-2-((((9H-fluoren-9-yl)methoxy) carbonyl)amino)-4-methylpentanamido)-2-(phenylthio)acetic acid (22)

A mixture of Fmoc-Leu-NH$_2$ (20) (1.0 g, 2.8 mmol) and glyoxylic acid monohydrate (0.3 g, 3.6 mmol) in methyl ethyl ketone (12 mL) was heated at 50° C. for 48 h. The solvent was evaporated under reduced pressure to yield 21 (1.2 g, crude) as colorless syrup, which was directly used for the next step without further purification.

A solution of 21 in acetic acid (17 mL) was cooled in ice and thiophenol (0.6 mL, 5.6 mmol) was added followed by 0.9 mL of sulfuric acid. After stirring at room temperature for two days, the mixture was poured into ice and extracted with ethyl acetate. The ethyl acetate solution was washed with saturated sodium bicarbonate, with water and dried over MgSO$_4$. The ethyl acetate was evaporated under reduced pressure and the residue was purified by RP-HPLC to give 22 (515 mg, 35% for two steps) as a white solid. ESI-MS m/z 541.18 (M+Na)$^+$.

Example 6

Synthesis of Resin Bound Tripeptide (25)

The resin bound tripeptide (25) was prepared on 2-chlorotrityl chloride resin (NovaBiochem, initial loading 1.51 mmol/g) using standard Fmoc SPPS protocols. To 120 mg (0.18 mmol) of 2-chlorotrityl chloride resin in a centrifuge tube is added 1.5 mL of $CH_2Cl_2$ and allowed to preswell for 10 min. Dipeptide 5 (100 mg, 0.19 mmol) and DIPEA (80 uL, 0.45 mmol) were added to the mixture and shaken 2 h at rt. The resin is washed thoroughly with $CH_2Cl_2$ and dried in vacuum to give dipeptide loaded 2-chlorotrityl resin 23 (200 mg).

The resin 23 (200 mg) is first swelled in DMF for 10 min and then deprotected with 10% piperidine in DMF (3 mL) solution for 10 min. The resin are filtered off and washed thoroughly with DMF, isopropyl alcohol and $CH_2Cl_2$. The following two coupling reactions are carried out using 4 equivalents of the Fmoc-Phe-OH (pyrazinoic acid for the second coupling), 4 equivalents of HBTU (TBTU for pyrazinoic acid), 4 equivalents of HOBt-$H_2O$, and 6 equivalents of DIPEA in $CH_2Cl_2$ (Active ester was formed by solution phase at 0° C. for 20 min). After two coupling reaction (2 h at room temperature), the resin was washed with DMF and $CH_2Cl_2$ to give resin bound tripeptide 25 (180 mg).

Example 7

Synthesis of a Pyz-Phe-Leu proteasome substrate bearing a dansyl fluorophore The resin 25 (60 mg) was mixed with a solution of AcOH/$CF_3CH_2OH$/$CH_2Cl_2$ (1/2/7, 1.0 mL) and the resultant suspension was shaken under argon at rt for 1.5 h. The resin was filtered and rinsed with $CH_2Cl_2$. After the combined filtrate and washing were concentrated in vacuo, the crude acid 26 was precipitated and triturated with chilled $Et_2O$, which was directly used for the coupling reaction without further purification. ESI-MS m/z 572.19 $(M+Na)^+$.

To a solution of 26 (10 mg, 0.018 mmol) in dry DMF (0.2 mL) were added DIPEA (2 uL, 0.011 mmol), dansyl ethylenediamine (6.5 mg, 0.022 mmol), EDC (4.2 mg, 0.022 mmol) and NHS (2.5 mg, 0.022 mmol). After stirring at room temperature overnight, the solvent was removed under reduced pressure and the residue was dissolved in DMSO and purified by RP-HPLC to give 3.5 mg (26% for two steps) of the Pyz-Phe-Leu proteasome substrate bearing a dansyl fluorophore. ESI-MS m/z 825.32 $(M+H)^+$.

Example 8

Synthesis of a Cbz-Leu-Leu-Leu proteasome substrate bearing a dansyl fluorophore The resin 23 (320 mg) was deprotected with 10% piperidine in DMF (3 mL) solution for 10 min. The resin was filtered off and washed thoroughly with DMF, isopropyl alcohol and $CH_2Cl_2$. The following coupling reaction was carried out using 4 equivalents of the Fmoc-Leu-OH and Cbz-Leu-OH, 4 equivalents of HBTU, 4 equivalents of HOBt-$H_2O$, and 6 equivalents of DIPEA in $CH_2Cl_2$ (Active ester was formed by solution phase at 0° C. for 20 min). After two coupling reaction (2 h at room temperature), the resin was washed with DMF and $CH_2Cl_2$ to give resin bound tetrapeptide 27 (280 mg).

The resin obtained above (125 mg) was cleaved with a solution of AcOH/$CF_3CH_2OH$/$CH_2Cl_2$ (1/2/7, 1.0 mL) and the resultant suspension was shaken under argon at rt for 1.5 h. The resin was filtered and rinsed with $CH_2Cl_2$. After the combined filtrate and washing were concentrated in vacuo, the crude acid 28 was precipitated and triturated with chilled $Et_2O$, which was directly used for the coupling reaction without further purification. ESI-MS m/z 657.33 $(M+H)^+$.

To a solution of 28 (28 mg, 0.043 mmol) in dry DMF (0.4 mL) were added DIPEA (4 uL, 0.026 mmol), dansyl ethylenediamine (15 mg, 0.051 mmol), EDC (10 mg, 0.051 mmol) and NHS (6.0 mg, 0.051 mmol). After stirring at room temperature overnight, the solvent was removed under reduced pressure and the residue was dissolved in DMSO and purified by RP-HPLC to give 12 mg (35% for two steps) of the Cbz-Leu-Leu-Leu proteasome substrate bearing a dansyl fluorophore. ESI-MS m/z 932.44 $(M+H)^+$.

Example 9

Ubiquitin Expression and Purification

UbΔG76 was cloned into the pTYB2 expression vector with a C-terminal intein-chitin binding domain tag (intein-CBD) and transformed into *E. coli* BL21 (DE3) cells. Cells harboring the UbΔG76-intein-CBD plasmid were grown in a 5 L fermentor to an OD of 25 and then expression of the fusion protein was induced at 20° C. for 18 hours with 0.5 mM IPTG. The cells were harvested by centrifugation at 5000 rpm for 20 minutes and the cell pellets frozen at −80° C. in 100 g aliquots. For purification, a frozen aliqout of the cells was suspended in 400 mL Tris buffered saline (50 mM Tris, 150 mM NaCl, pH 6.5) and lysed via sonication. The soluble fraction was isolated by centrifugation at 13,000 rpm for 30 minutes and loaded onto a 100 mL chitin-agarose column (New England BioLabs) at room temperature. The column was washed with 5-10 column volumes (CV) of TBS to remove unbound proteins. In order to cleave the C-terminal Ub-intein thioester bond, 1.5 CV of TBS containing 100 mM sodium mercaptoethane sulfonate (MESNa) was added to the matrix and the resultant slurry incubated at room temperature overnight. UbΔG76-MESNa was eluted with TBS and concentrated using a centrifugal concentrator (3000 MWCO). UbΔG76-MESNa was desalted and further purified by RP-HPLC on a semi-preparative Viva C8 column (21×150 mm, Restek) using standard TFA/acetonitrile buffers. Peak fractions were pooled and neutralized with triethylamine (TEA). Acetonitrile was evaporated under a stream of $N_2$, and the sample divided into aliquots and lyophilized. The lyophilized samples were stored at −80° C.

Example 10

Chemical Modification of Ubiquitin

Figure 3:
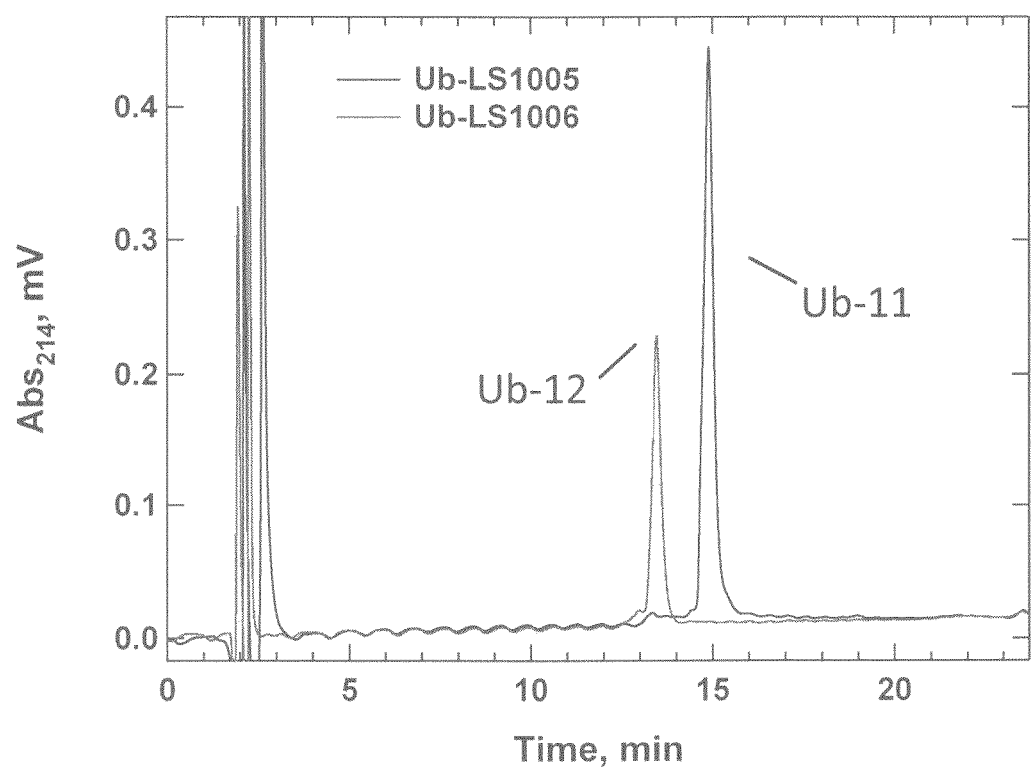
FIG. 3 shows representative RP-HPLC chromatograms of certain substrates of the invention.

Prior to conjugation, the UbΔG76-MESNa was redissolved in PBS, pH 6.5 and residual TFA removed by chromatography on a GE Healthcare PD10 column equilibrated in PBS. The sample was concentrated as above (10 mg/mL). The compounds of Examples 1-4 were dissolved in DMSO at a concentration of 0.2-0.4 M and added to the UbΔG76-MESNa at a 140-180:1 molar ratio. Reaction progress was monitored by analytical RP-HPLC on a Viva C8 column (4.6×150 mm, Restek). Aliquots of each sample were injected onto the column equilibrated in 20% $CH_3CN$/0.1% TFA at 1 mL/min. The column was developed with a gradient to 50% $CH_3CN$/0.1% TFA over 20 minutes. C-terminally modified Ub was purified by semi-preparative RP-HPLC as described above. Peak fractions were pooled and neutralized with $NH_4HCO_3$. The acetonitrile was removed by evaporation under a stream of $N_2$, and the sample was divided into aliquots and lyophilized. The purified, chemically modified Ub substrates, i.e., Ub-10, Ub-11, Ub-12 and Ub-19, were analyzed by analytical RP-HPLC and ESI-MS. The results of this analysis are set forth in Table 5 and FIG. 3.

TABLE 5

Analysis of Ubiquitin probes

| Conjugate | Expected mass | Measured mass |
|---|---|---|
| UbΔG76 | 8507.8 | 8507. |
| UbΔG76-MES (minus Na⁺) | 8632 | 8632 |
| Ub-10 | 8978 | 8979 |
| Ub-11 | 9005 | 9006 |
| Ub-12 | 8998 | 8999 |
| Ub-19 | 8999 | 9000 |

Example 11

Figure 4:
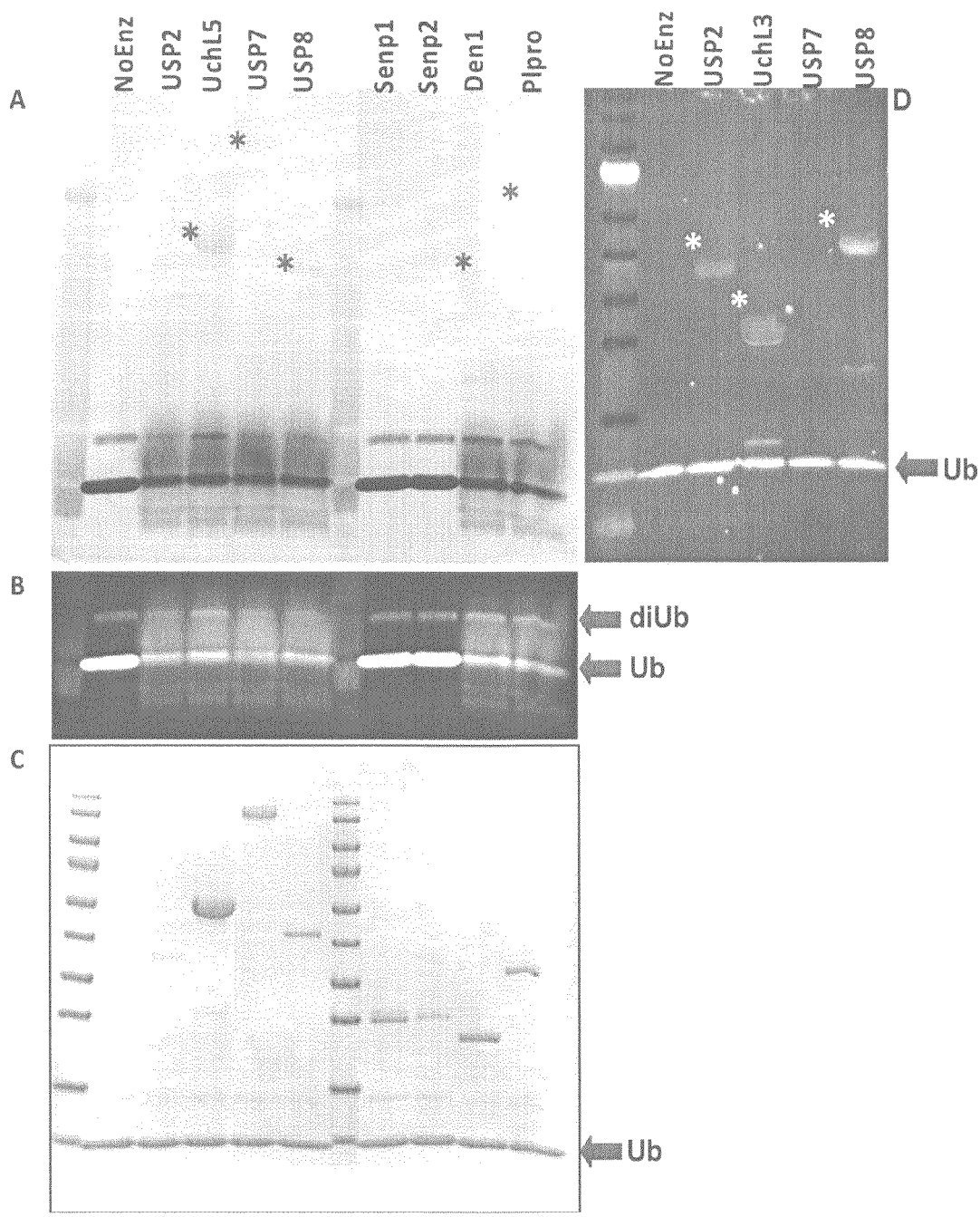
FIG. 4 shows the results of SDS-PAGE analyses following digestions of dansyl-labeled and biotin-labeled substrates of the invention by various DUBs. A and B are fluorescent images captured under long wavelength UV irradiation. A is an inverted image which had the brightness and contrast adjusted to improve visualization of the labeled DUBs, whereas B is a normal image with brightness and contrast adjusted to emphasize loss of intensity in the substrate band after digestion. C is an image of the same gel stained with Coomassie Blue. D shows the visualization of a biotinylated substrate with fluorescein conjugated avidin using $\lambda_{Ex}$=460 nm and $\lambda_{Em}$=515 nm. Labeled DUBs are indicated with stars.
Figure 5:
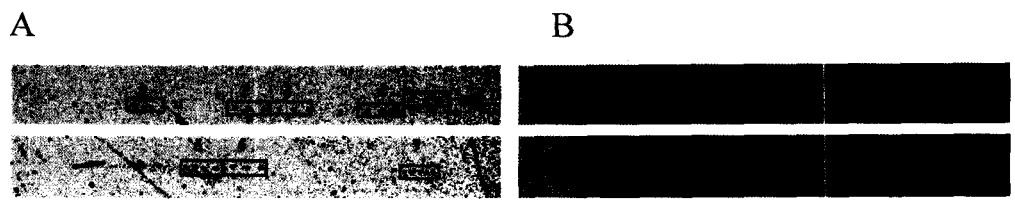
FIG. 5 shows the results of microarray-based assays using substrates of the invention. A-Ub-11 (Example 2). Labeled spots were visualized directly for dansyl fluorescence ($\lambda_{Ex}$=420 nm, $\lambda_{Em}$=535 nm). B-Ub-12 (Example 3). Labeled spots were visualized following reaction with fluorescein conjugated avidin ($\lambda_{Ex}$=532 nm and $\lambda_{Em}$=610 nm).

Demonstration that Chemically-Modified Ubiquitin Functions as a Substrate for DUBs In order to test the compounds prepared in Example 10 as substrates for DUBs, two types of experiments were performed; a liquid phase assay and a microarray-based assay.

a. Liquid Phase Assay:

Equal volumes of the chemically-modified UB substrates and DUB's were mixed in assay buffer and incubated at 37° C. for 1 hr. Digestions were stopped by the addition of SDS-PAGE sample buffer±reducing agent. The DUBs chosen were: USP2core, UCH-L3 or UCH-L5, USP7, USP8, Senp1, Senp2, DEN1, and PLPro, USP2core, UCH-L3, USP7 and USP8 are well characterized deubiquitylases. Both DEN1 and PLPro were originally described as deubiquitylases although they were later shown to have higher activity towards Nedd8 and ISG15, respectively. Senp1 and Senp2 are desumoylases. For Ub-10-12, the Schiff base formed from the reaction of the aldehyde (produced on decomposition of the α-substituted glycine) with primary amines in the protein were reduced to amides with NaBH$_3$CN (1 mM). The digests were resolved on 10-20% polyacrylamide gradient gels. Representative results for two substrates Ub-11 and Ub-19 are shown in FIG. 4. For digestions with Ub-10 (not shown) and Ub-11, the gels were immediately visualized under UV illumination (FIGS. 4A and B) and then stained with Coomassie Blue (FIG. 4C). For digestions containing Ub-12 (not shown) and Ub-19, the proteins were electroblotted onto PVDF membranes, which were then blocked with fish gelatin in Tris-buffered saline containing 0.1% Tween20 (TBST) and reacted with an avidin-fluorescein conjugate (ThermoFisher). The blots were washed with 3 changes of TBST to remove unbound avidin and then fluorscein fluorescence visualized by exposure to 460 nm light (FIG. 4D). All four modified ubiquitins were cleaved by enzymes expected to have deubiquitylase activity (lanes 3-6, 10, and 11) but not by the two desumoylases (lanes 8 and 9). This is especially apparent in FIG. 4B in which a clear decrease in the fluorescence intensity in the ubiquitin band can be seen as well as an increase in diffuse fluorescence resulting from aberrant migration of released fluorophore. When using Ub-11 and Ub-12, which generate an aldehyde following cleavage and decomposition of the α-substituted glycine, transfer of the label (DNS or biotin) occurred at low efficiency. The faint bands highlighted by red stars in FIG. 4A are consistent with the migration positions of the respective DUBs. Reaction with the aldehyde will generate a Schiff base, which is unstable. Furthermore, the reaction is concentration dependent and pH dependent. In all of the digestions shown, the concentration of the substrates was limiting.

b. Microarray-Based Assay:

Since one of the primary uses for the substrates of the invention is localization of active deubiquitylases immobilized in a microarray-type format, i.e. solid phase assay, each of the substrates was tested for its ability to be cleaved and subsequently transfer label to DUBs immobilized on a Nexterion slide H (Schott). Thirty-five (35) DUBs were arrayed as a series of triplicate spots on the slide (see Table 6 for a map of the array) Three identical arrays were constructed on each slide. Representative results for Ub-11 and Ub-12 are shown in FIG. 5. Several features that were common amongst each array on a given slide and between slides are shown boxed in red and numbered 1-7. They are: USP2core (1); USP28 (2); DEN1 (3); JOSD1 (4); AMSH (5); USP8core (6); and Ataxin3-like (7). These features also gave positive signals with Ub-10 (data not shown). When the same analysis was performed using ubiquitin-vinylsulfone (data not shown), all of the immobilized proteins were labeled; hence, the substrates of the invention exhibit higher specificity than Ub-vinylsulfone in this format. It should be noted that the enzymes (and antibodies) were coupled 1) at different concentrations and 2) by covalent attachment through surface exposed lysines. It cannot be said at this time whether these conditions would preserve the activity of the enzymes, but the data in FIG. 5 suggest that this is the case for at least 7 enzymes.

The experimental results described above show that each of the chemically-modified Ubs tested were functional substrates for at least 6 enzymes with deubiquitylase activity in a liquid phase assay, and did not show significant cleavage by two desumoylases under identical conditions. Furthermore, in the testing of chemically-modified Ub using a microarray formed with 35 individual enzymes, seven enzymes were labeled on the microarrays including three of the enzymes tested in the liquid-phase assay.

Example 12

Fluorescently-Labeled Pyz-Phe-Leu Functions as a Substrate for the Proteasome

Figure 6:
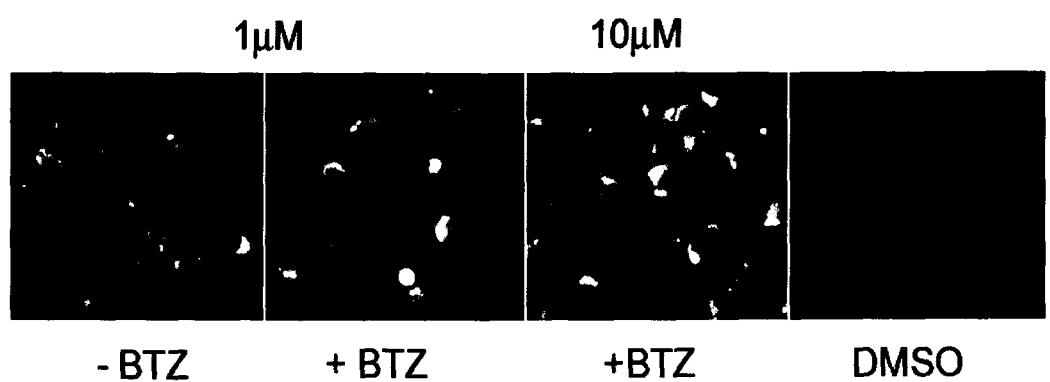
FIG. 6 shows the results of dose-dependent peri nuclear staining by the Pyz-Phe-Leu proteasome substrate consistent with the expected localization of proteasomes in HCT116 cells (+BTZ=Bortezomib Pre-treated; −BTZ=No Bortezomib Pre-treatment; DMSO=dimethylsulfoxide).

In order to test the compound described in Example 7 as a cell permeable proteasome substrate, HCT116 cells (1.25× 10$^5$) were grown on 10 mm polylysine coated coverslips for 24 hrs in DMEM supplemented with 10% FCS. Cells were pre-treated with Bortezomib (50 nM) for 1 hr followed by the incubation with Pyz-Phe-Leu proteasome substrate (1 uM and 10 uM final concentrations) for an additional 1 hr. Each coverslip was washed three times with PBS and fixed in 4% paraformaldehyde/PBS, pH, 7.2. Digital fluorescent imaging was done using Lieca upright florescent microscope DMR-BE equipped with CCD camera and 40× objective. The results shown in FIG. 6 clearly show dose-dependent perinuclear staining consistent with the expected localization of proteasomes in these cells.

A number of patent and non-patent publications are cited throughout the foregoing specification in order to describe the state of the art to which this invention pertains. The entire disclosure of each of these citations is incorporated by reference herein.

While certain embodiments of the present invention have been described and/or exemplified above, various other embodiments will be apparent to those skilled in the art upon review of the foregoing disclosure. The present invention is, therefore, not limited to the particular embodiments described and/or exemplified, but is capable of considerable variation and modification without departure from the scope of the appended claims. Furthermore, the transitional phrases "comprising", "consisting essentially of" and "consisting of", when used in the appended claims, in original and amended form, define the claim scope with respect to what unrecited additional claim elements or steps, if any, are excluded from the scope of the claim. The term "comprising" is intended to be inclusive or open-ended and does not exclude additional, unrecited elements, method steps or materials. The phrase "consisting of" excludes any element, step or material other than those specified in the claim, and, in the latter instance, impurities ordinarily associated with the specified materials. The phrase "consisting" essentially of limits the scope of a claim to the specified elements, steps or materials and those that do not materially affect the basic and novel characteristic(s) of the claimed invention. All compositions or formulations identified herein can, in alternate embodiments, be more specifically defined by any of the transitional phrases "comprising", "consisting essentially of" and "consisting of".

TABLE 6

| AMSH core | USP7 | USP2 core | PLP2 | USP28 | DEN1 | Otub1 | JosD1 | α-hIgG Bap1 |
|---|---|---|---|---|---|---|---|---|
| Ubch 7 | HDM2 | α-USP15 | α-DEN1 | α-UCH L3 | α-JosD1 | α-Senp6 | α-Senp1 | α-AMSH α-IgY |
| UCH L3 | USP34 | USP51 | PLPro | USP8 | Senp1 | UCH L3 | JOSD2 | UCH L5 |
| Ubc13 | Murf 1 | α-Ub | α-USP14 | α-UCH L5 | α-ATX3-like | | α-USP8 | α-USP4 | α-JosD2 |
| UCH L5 | USP51 core | USP14 | Senp2 | UBP43 | Senp6 | Ataxin3 | UCH L1 | Buffer Otub2 |
| Msm2 | Prajal | E6AP | Pre-imm. | α-USP5 | α-Senp2 | α-Otub1 | α-PLPro | α-USP34 empty |
| YOD1 | USP4 | USP20 | AMSH | USP8 core | Senp2 | SH3 | Ulp1 | Atx3-like |
| Ubch5c | E2-25K | CARP2 | α-PLP2 | α-Otub2 | α-UCHL1 | | α-USP2 | α-SSEL | α-Ataxin3 |

What is claimed is:

1. A synthetic protease substrate of the formula

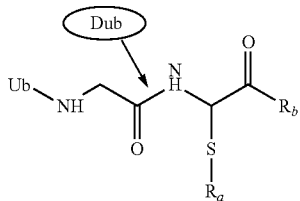

wherein $R_a$ is selected from the group H, alkyl ($C_1$-$C_{10}$), aryl ($C_6$-$C_{14}$), L-Fl, and L-Biot, wherein L represents a linker, -A-NH—, in which A represents an alkylene moiety, ($C_1$-$C_{10}$), a heteroalkylene moiety ($C_1$-$C_{10}$), an arylene moiety ($C_6$-$C_{14}$), or an aralkylene moiety ($C_7$-$C_{20}$) Fl represents a fluorophore and Biot represents a biotinyl group; $R_b$ is selected from the group of hydroxy, alkoxy ($C_1$-$C_{10}$), -L'-Fl and -L'-Biot, wherein L' represents a linker, —NH—X—NH—, in which X represents an alkylene ($C_1$-$C_{10}$), cycloalkylene ($C_3$-$C_{10}$), arylene ($C_6$-$C_{14}$), aralkylene ($C_7$-$C_{20}$) or heteroarylene moiety ($C_6$-$C_{10}$), Fl represents a fluorophore and Biot represents a biotinyl group, wherein Ub is a ubiquitin moiety, a ubiquitin-like protein moiety Cbz-Leu-Leu-Leu or Pyz-Phe-Leu; and the arrow indicates a bond cleavable by a de-ubiquitylating enzyme (DUB).

2. A substrate according to claim 1 of the formula:

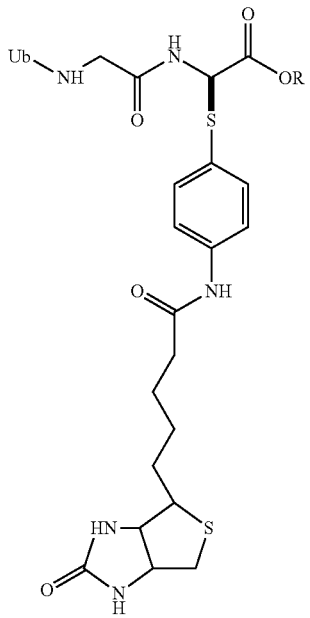

wherein R represents H or alkyl ($C_1$-$C_{10}$).

3. A substrate according to claim 1 of the formula:
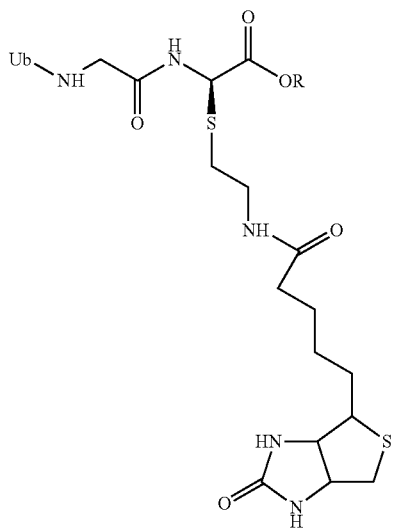
wherein R represents H or alkyl ($C_1$-$C_{10}$).
4. A substrate according to claim 1 of the formula:
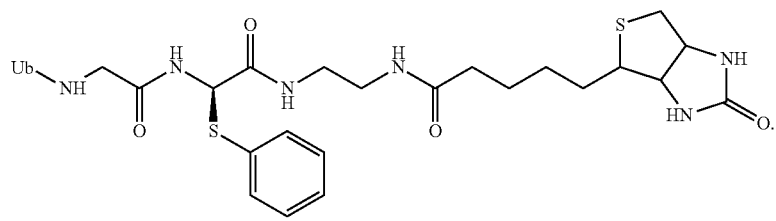
5. A substrate according to claim 1 of the formula:
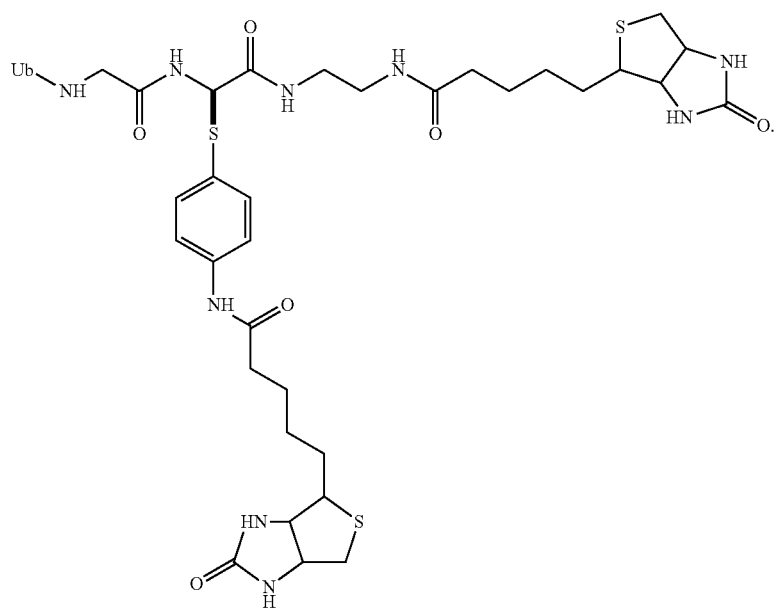
6. A substrate according to claim 1 of the formula:
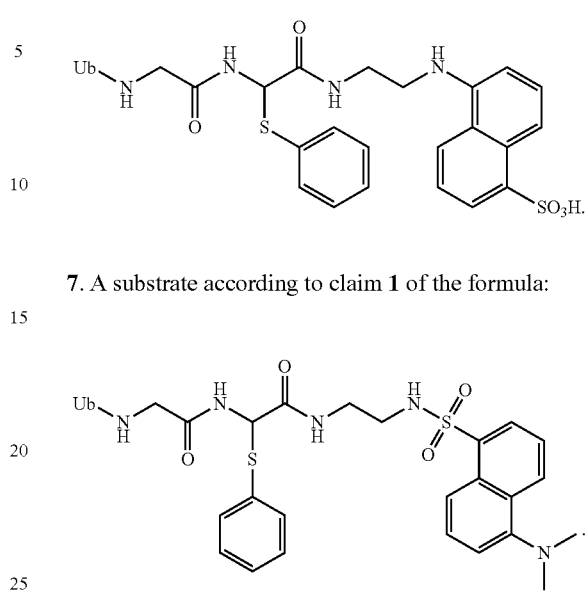
7. A substrate according to claim 1 of the formula:

8. A method for determining de-ubiquitylating activity comprising:
(a) exposing the substrate of claim 1 to a DUB under conditions suitable for cleavage of the —S—$R_a$ moiety and the —C(=O)—$R_b$ moiety from said substrate; and
(b) detecting the occurrence of cleavage from said substrate of at least one of a reactive thiol compound comprising the —S—$R_a$ moiety and a reactive glyoxal compound comprising the —C(=O)—Rb moiety.

9. The method of claim 8, further comprising the step of capturing at least one of said compounds on a capture device comprising a solid support on which a capture agent is immobilized, said capture agent having functional groups that form covalent or non-covalent chemical bonds with at least one of said reactive thiol compound and said reactive glyoxal compound; and wherein the detecting step comprises detecting a reporter moiety present on said capture device, the amount of reporter moiety detected being proportional to the amount of said DUB.

10. The method according to claim 9, wherein the Ub moiety of said substrate represents ubiquitin and said substrate is exposed to an isopeptidase.

11. The method according to claim 9, wherein the Ub moiety is Cbz-Leu-Leu-Leu and said substrate is exposed to a proteasome.

12. The method according to claim 9, wherein the Ub moiety is Pyz-Phe-Leu and said substrate is exposed to a proteasome.

13. The method according to claim 9, wherein said —C(=O)—$R_b$ moiety comprises a detectable reporter moiety.

14. The method according to claim 13, wherein the compound comprising the C(=O)—$R_b$ moiety is the reactive glyoxal compound which forms a chemical bond with amine functional groups of said capture device in the presence of $NaCNBH_3$.

15. The method according to claim 14, wherein said capture agent comprises a protein selected from bovine serum albumin or hen ovalbumin.

16. The method according to claim 9, wherein said substrate is exposed to said DUB in a vessel which contains said capture device.

17. The method according to claim 9, wherein said substrate is exposed to said DUB in a first vessel and is transferred to a second vessel which contains said capture device.

18. The method according to claim 9, wherein said DUB is co-immobilized on said solid support with said capture agent.

19. The method according to claim 18, wherein said solid support is a multi-well microtiter plate.

20. The method according to claim 19, wherein the Ub of the substrate that is exposed to DUB in one well of said microtiter plate is distinct from the Ub of the substrate that is exposed to DUB in any well of said microtiter plate adjacent to said one well.

21. The method according to claim 18, wherein said solid support is a microarray of different proteases immobilized at discrete locations on said support.

22. The method according to claim 9, wherein at least one of said —S—$R_a$ and —C(=O)—$R_b$ moieties comprises a biotinyl group as said detectable reporter moiety.

23. The method according to claim 22 further comprising coupling said biotinyl group to labeled streptavidin and detecting said label.

24. The method according to claim 23, wherein said streptavidin has a fluorescence label which is detected by fluorescence assay.

25. The method according to claim 22, wherein said streptavidin has a color-producing enzyme label which is detected by colorimetric assay.

26. The method according to claim 8, wherein said —S—$R_a$ and —C(=O)—$R_b$ moieties comprise different fluorescent labels, said labels forming a Förster Resonance Energy Transfer (FRET) pair, and the occurrence of cleavage of at least one of said —S—$R_a$ and —C(=O)—$R_b$ moieties is detected by measuring a variation in relationship between the members of said FRET pair.

27. The method according to claim 8, wherein said —S—$R_a$ and —C(=O)—$R_b$ moieties comprise at least one fluorescent label, and wherein the occurrence of cleavage of at least one of said —S—$R_a$ and —C(=O)—$R_b$ moieties is detected by fluorescence spectroscopy.

28. The method according to claim 27, wherein the DUB is within a cell.

29. The method according to claim 28, wherein the cell is an HCT116 cell.

30. A method for determining de-ubiquitylating activity in a plurality of cells by flow cytometry comprising:
(a) exposing the substrate of claim 1 to a plurality of cells containing at least one DUB under conditions suitable for cleavage of —S—$R_a$ and —C(=O)—$R_b$, wherein said —S—$R_a$ and —C(=O)—$R_b$ moieties comprise at least one fluorescent label; and
(b) detecting by said flow cytometry the cells which exhibit by fluorescence the occurrence of cleavage of at least one of said —S—$R_a$ and —C(=O)—$R_b$ moieties.

31. The method according to claim 30, further comprising the step of calculating the number of cells of said plurality which demonstrate DUB activity.

32. An assay kit comprising at least one synthetic substrate as claimed in claim 1, and, as a positive control, at least one DUB capable of cleaving said substrate and yielding at least one of a reactive thiol compound comprising the —S—$R_a$ moiety and a reactive glyoxal compound comprising the —C(=O)—$R_b$.

33. An assay kit as claimed claim 32 further comprising a solid support carrying a microarray of said DUB(s).

* * * * *